US 8,470,766 B2

(12) United States Patent
Kilpatrick et al.

(10) Patent No.: US 8,470,766 B2
(45) Date of Patent: Jun. 25, 2013

(54) PROTEIN KINASE C THERAPY FOR THE TREATMENT OF ACUTE LUNG INJURY

(75) Inventors: Laurie Ellen Kilpatrick, Narberth, PA (US); Helen Marie Korchak, Bryn Mawr, PA (US); Clifford S. Deutschman, Narbeth, PA (US)

(73) Assignees: The Children's Hospital of Philadelphia, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 440 days.

(21) Appl. No.: 12/488,954

(22) Filed: Jun. 22, 2009

(65) Prior Publication Data

US 2010/0003199 A1    Jan. 7, 2010

Related U.S. Application Data

(63) Continuation-in-part of application No. PCT/US2007/088754, filed on Dec. 22, 2007.

(60) Provisional application No. 60/871,658, filed on Dec. 22, 2006.

(51) Int. Cl.
    *A61K 38/08* (2006.01)

(52) U.S. Cl.
    USPC ............. 514/1.4; 514/1.5; 514/1.6; 514/1.7; 514/21.6

(58) Field of Classification Search
    None
    See application file for complete search history.

(56) References Cited

U.S. PATENT DOCUMENTS

| | | | |
|---|---|---|---|
| 6,526,976 B1* | 3/2003 | Baran | 128/207.14 |
| 6,855,693 B2* | 2/2005 | Mochly-Rosen et al. | 530/324 |
| 2004/0259816 A1* | 12/2004 | Pandol et al. | 514/27 |
| 2006/0019256 A1 | 1/2006 | Clarke et al. | |
| 2007/0117164 A1 | 5/2007 | Raskov et al. | |

OTHER PUBLICATIONS

Abraham ("Neutrophils and acute lung injury." Crit. Care Med., 2003, 31, S195-S199).*
Kilpatrick et al. ("A role for PKC-δ and Pi 3-kinase in TNF-α-mediated antiapoptotic signaling in the human neutrophil." Am. J. Physiol. Cell Physiol. 2002, 283, C48-C57).*
Wang K. et al. ("Inhibition of neutrophil apoptosis by type 1 IFN depends on cross-talk between phosphoinositol 3-kinase, protein kinase C-δ, and NF-κ B signaling pathways." J. Immunol. 2003, 171, 1035-1041).*
Kilpatrick et al. ("Selective regulation by δ-PKC and PI 3-kinase in the assembly of the antiapoptotic TNFR-1 signaling complex in neutrophils." Am. J. Physiol. Cell Physiol., 2004, 287, C633-C642).*
Chen, L., et al. "Opposing cardioprotective actions and parallel hypertrophic effects of delta PKC and epsilon PKC." Proc Natl Acad Sci U S A. Sep. 25, 2001;98(20):11114-9. Epub Sep. 11, 2001.
Direct Inhibition of delta-Protein Kinase C Enzyme to Limit Total Infarct Size in Acute Myocardial Infarction (DELTA MI) Investigators, et al. "Intracoronary KAI-9803 as an adjunct to primary percutaneous coronary intervention for acute ST-segment elevation myocardial infarction." Circulation. Feb. 19, 2008;117(7):886-96. Epub Feb. 4, 2008.
Kaneda, H., et al. "Preserved coronary endothelial function by inhibition of delta protein kinase C in a porcine acute myocardial infarction model." Int J Cardiol. Apr. 3, 2009;133(2):256-9. Epub Feb. 1, 2008.
Chou, W., et al. "Neutrophil protein kinase Cdelta as a mediator of stroke-reperfusion injury." J Clin Invest. Jul. 2004;114(1):49-56.
Qi, X., et al. "Sustained pharmacological inhibition of deltaPKC protects against hypertensive encephalopathy through prevention of blood-brain barrier breakdown in rats." J Clin Invest. Jan. 2008;118(1):173-82.
Shukla, A., et al. "Asbestos-induced peribronchiolar cell proliferation and cytokine production are attenuated in lungs of protein kinase C-delta knockout mice." Am J Pathol. Jan. 2007;170(1):140-51.

* cited by examiner

*Primary Examiner* — Christina Bradley
(74) *Attorney, Agent, or Firm* — Dan, Dorfman, Herrell & Skillman; Kathleen D. Rigaut

(57) ABSTRACT

The present invention provides novel formulations of a δPKC inhibitor. The δPKC inhibitor can be, for example, a peptide. The present invention also discloses a method of preventing acute pulmonary cell injury associated with trauma, ALI or ARDS and a method of inhibiting an inflammatory response in pulmonary cells by inhibiting the activity of δPKC. The invention also provides a method of treating a pulmonary disease with an aerosol formulation of a δPKC inhibitor to inhibit neutrophil activity.

7 Claims, 21 Drawing Sheets

Regulation of TNF Signaling by δ-PKC in Adherent Neutrophils

```
              δV1.1                              δV1.2
δPKC  MAPFLRISF NSYELGSLQA   EDDASQPFCA  VKMKEALTTD  RGKTLVQKKP
θPKC  MSPFLRIGL SNFDCGSCQS   CQGEAVNYPCA VLVKEYVESE  NGQMYIQKKP

δPKC  TMYPEWKSTF DAHIYEGRVI  QIVLMRAAED  PMSEVTVGVS  VLAERCKKNN
θPKC  TMYPPWDSTF DAHINKGRVM  QIIVKGKNVD  LISETTVELY  SLAERCRKNN

δPKC  GKAEFWLDL QPQAKVLMCV   QYFLE       = SEQ ID NO: 6
θPKC  GKTEIWLEL KPQGRMLMNA   RYFLE       = SEQ ID NO: 7
```

B

SEQ ID NO: 1:  SFNSYELGSL   (amino acids 8-17 of δPKC)

SEQ ID NO: 2:  YGRKKRRQRRR  (amino acids 47-57 of Tat)

C

SEQ ID NO: 3:  AFNSYELGSL   (amino acids 8-17 of human δPKC)

Effect of 2CLP on Lung Pathology

Figure 7
2CLP Activates NFκB in Rat Lungs
A.
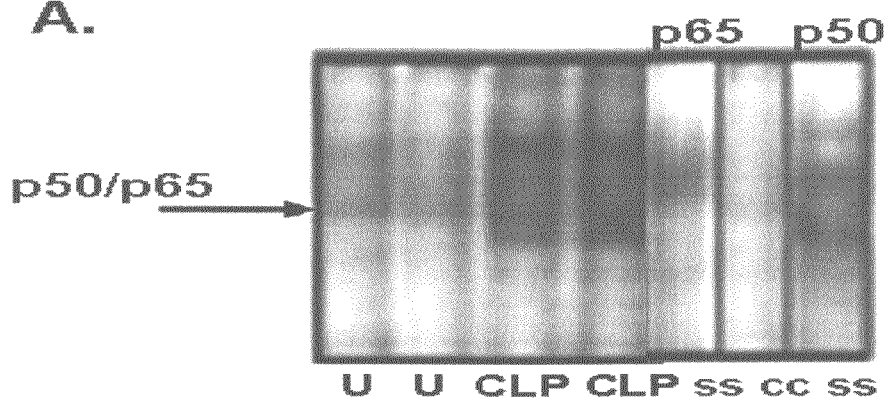
B.

2CLP increases NFκB-dependent CINC-1 and IL-6 expression in whole lung homogenates TNF Mediated Supression of Caspase 3
Activity: Role for δ-PKC Role of δ-PKC in TNF Mediated Assembly
of TNFR-1 Signaling Complex TNF Mediated O2- Generation in
Adherent Neutrophils: Role of δ-PKC Effect of Intra-tracheal
Administration of δ-PKC-TAT Peptide
Inhibitor on Total Protein
Concentration in BALF Following 2CLP Measurement of δ-PKC levels in
Leukocytes from BALF Samples in a Rat
Model of ARDS

2CLP　　　　　2CLP
+PBS　　　　+δ-PKC-TAT

Intra-tracheal Administration of the δ-PKC
TAT Peptide Inhibitor Blocks 2CLP-Mediated
Phosphorylation of δ-PKC(Thr505) in the Lung Intra-tracheal Administration of the δ-PKC TAT Peptide Inhibitor Decreases 2CLP-Mediated Elevations of the Chemokines CINC-1 and MIP-2 in the Lung Intra-tracheal Administration of the δ-PKC TAT Peptide Inhibitor Decreases 2CLP-Mediated Elevations of Plasma CINC-1 and MIP-2

Intra-tracheal Administration of δ-PKC-TAT Peptide Inhibitor Decreases Sepsis-induced Lung Injury 24 hrs Following 2CLP

δ-PKC TAT Inhibitory Peptide Target Site in Lung

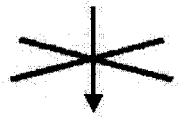

1. Activation of NFκB
2. Synthesis of Chemokines (CINC-1)
3. Upregulation of Adhesion Molecules (ICAM-1)

B

δ-PKC TAT Inhibitory Peptide Target Site Pulmonary Neutrophils

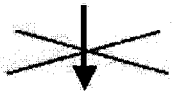

1. Neutrophil Migration
2. Neutrophil Apoptosis
3. Neutrophil β-integrin Expression

C

δ-PKC TAT Inhibitory Peptide Target Site

↓

Lung

↓

Pulmonary Neutrophils

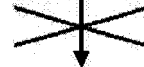

1. Infiltration of Inflammatory Cells
2. Myeloperoxidase Activity
3. Pulmonary Edema
4. Lung Tissue Destruction

SEQUENCE LISTING

```
<160> NUMBER OF SEQ ID NOS: 7

<210> SEQ ID NO 1
<211> LENGTH: 10
<212> TYPE: PRT
<213> ORGANISM: Rat

<400> SEQUENCE: 1

Ser Phe Asn Ser Tyr Glu Leu Gly Ser Leu
1               5                   10

<210> SEQ ID NO 2
<211> LENGTH: 11
<212> TYPE: PRT
<213> ORGANISM: Human

<400> SEQUENCE: 2

Tyr Gly Arg Lys Lys Arg Arg Gln Arg Arg
1               5                   10

<210> SEQ ID NO 3
<211> LENGTH: 10
<212> TYPE: PRT
<213> ORGANISM: Human

<400> SEQUENCE: 3

Ala Phe Asn Ser Tyr Glu Leu Gly Ser Leu
1               5                   10
```

-continued

<210> SEQ ID NO 4
<211> LENGTH: 25
<212> TYPE: RNA
<213> ORGANISM: Rat

<400> SEQUENCE: 4
ccacuacauc aagaaccaug aguuu                                              25

<210> SEQ ID NO 5
<211> LENGTH: 25
<212> TYPE: DNA
<213> ORGANISM: Rat

<400> SEQUENCE: 5
tcgagagatg gggaatcccc agccc                                              25

<210> SEQ ID NO 6
<211> LENGTH: 123
<212> TYPE: PRT
<213> ORGANISM: Rat

<400> SEQUENCE: 6

Met Ala Pro Phe Leu Arg Ile Ser Phe Asn Ser Tyr Glu Leu Gly Ser
 1               5                  10                  15

Leu Gln Ala Glu Asp Asp Ala Ser Gln Pro Phe Cys Ala Val Lys Met
            20                  25                  30

Lys Glu Ala Leu Thr Thr Asp Arg Gly Lys Thr Leu Val Gln Lys Lys
        35                  40                  45

Pro Thr Met Tyr Pro Glu Trp Lys Ser Thr Phe Asp Ala His Ile Tyr
    50                  55                  60

Glu Gly Arg Val Ile Gln Ile Val Leu Met Arg Ala Ala Glu Asp Pro
65                  70                  75                  80

Met Ser Glu Val Thr Val Gly Val Ser Val Leu Ala Glu Arg Cys Lys
                85                  90                  95

Lys Asn Asn Gly Lys Ala Glu Phe Trp Leu Asp Leu Gln Pro Gln Ala
            100                 105                 110

Lys Val Leu Met Cys Val Gln Tyr Phe Leu Glu
        115                 120

<210> SEQ ID NO 7
<211> LENGTH: 124
<212> TYPE: PRT
<213> ORGANISM: Mouse

<400> SEQUENCE: 7

Met Ser Pro Phe Leu Arg Ile Gly Leu Ser Asn Phe Asp Cys Gly Ser
 1               5                  10                  15

Cys Gln Ser Cys Gln Gly Glu Ala Val Asn Tyr Pro Cys Ala Val Leu
            20                  25                  30

Val Lys Glu Tyr Val Glu Ser Glu Asn Gly Gln Met Tyr Ile Gln Lys
        35                  40                  45

Lys Pro Thr Met Tyr Pro Pro Trp Asp Ser Thr Phe Asp Ala His Ile
    50                  55                  60

Asn Lys Gly Arg Val Met Gln Ile Ile Val Lys Gly Lys Asn Val Asp
65                  70                  75                  80

Leu Ile Ser Glu Thr Thr Val Glu Leu Tyr Ser Leu Ala Glu Arg Cys
                85                  90                  95

```
Arg Lys Asn Asn Gly Lys Thr Glu Ile Trp Leu Glu Leu Lys Pro Gln
            100                 105                 110

Gly Arg Met Leu Met Asn Ala Arg Tyr Phe Leu Glu
        115                 120
```

PROTEIN KINASE C THERAPY FOR THE TREATMENT OF ACUTE LUNG INJURY

This application is a continuation-in-part of PCT/US07/88754, filed Dec. 22, 2007. This application also claims the benefit of priority under 35 U.S.C. §119(e) to U.S. Provisional Patent Application 60/871,658, filed on Dec. 22, 2006. The disclosures of the foregoing applications are incorporated by reference in their entirety.

Pursuant to 35 U.S.C. §202(c), it is acknowledged that the United States Government has certain rights in the invention described herein, which was made in part with funds from the National Institutes of Health Grant No. R01 GM064552, and R01 AI024840.

FIELD OF THE INVENTION

The present invention relates to the fields of medicine, molecular biology and the treatment of disease. More specifically, the invention provides aerosolized compositions and methods for treating an inflammatory lung disease.

BACKGROUND OF THE INVENTION

Several publications and patent documents are cited throughout the specification in order to describe the state of the art to which this invention pertains. Each of these citations is incorporated herein by reference as though set forth in full.

A variety of pulmonary diseases are associated with inflammation, including acute and chronic diseases. Pulmonary diseases that are associated with inflammation include, for example, asthma, emphysema, acute lung injury (ALI) and adult respiratory distress syndrome (ARDS). Many of the lung diseases associated with inflammation have a significant effect on productivity, quality of life and overall physical health. For example, there are approximately 200,000 cases of ARDS in the United States, which manifest following systemic or pulmonary insults. Thus, inflammatory lung disease has a major impact on health care.

The early stages of an inflammatory response involve the release of chemotactic molecules that recruit inflammatory cells to the site of inflammation. Following injury or infection, inflammation produces critical alterations in neutrophil activity that can trigger the development of ALI and ARDS. Central to the destructive capacity of neutrophils is the activation of proinflammatory signaling (i.e. the release of reactive oxygen intermediates, nitric oxide, proteases, matrix metalloproteinases, cytokines, etc.) and the suppression or delay of neutrophil programmed cell death. Neutrophils are endstage cells and undergo apoptosis upon release into the circulation. However, during inflammatory diseases, neutrophil apoptosis is suppressed (Jimmenez, M. et al. (1997) Arch. Surg. 132: 1263-1269; Taneja, R. et al (2004) Crit. Care Med. 32:1460-1469). Enhanced neutrophil survival at the site of inflammation promotes increased bactericidal activity and can also result in acute inflammatory damage. Tumor Necrosis Factor (TNF) and other proinflammatory cytokines are important regulators of neutrophil function during such inflammatory responses through activation of proinflammatory signaling and are involved in the suppression of neutrophil apoptosis (Kilpatrick, L. et al. (2002) Am. J. Physiol. Cell Physiol. 283:C48-57; Lee, A. et al. (1993) J. Leukoc. Biol. 54:282-288).

Some lung diseases associated with inflammation can be treated, for example, with anti-inflammatory agents such as corticosteroids. However, corticosteroids have disadvantages. For example, corticosteroids can cause complete immunosuppression and can also induce "wasting" syndrome, diabetes, hypertension, peptic ulcer, osteoporosis, fatty liver, cataracts and other undesirable side effects.

There exists a need for safe and effective anti-inflammatory agents that reduce the severity of lung diseases associated with inflammation. The present invention satisfies this need and provides related advantages as well.

SUMMARY OF THE INVENTION

In accordance with the present invention, a composition of matter comprising an inhibitor of pulmonary neutrophil activation contained in an aerosolized formulation is provided. In a particularly preferred embodiment, the inhibitor comprises a peptide portion PKC, isotype delta fused in frame with an HIV-Tat peptide, e.g., δV1.1 PKC-Tat. The peptides of the invention may be administered alone or may be combined with other agents conventionally employed to treat pulmonary dysfunction.

In yet another aspect of the invention, a method of treating lung disease, comprising administering an effective amount of δV1.1 PKC-Tat to the lungs of a patient is disclosed. Such lung diseases include, without limitation, acute lung injury, adult respiratory distress syndrome, acute trauma, asthma, interstitial lung disease, emphysema, chronic bronchitis, cystic fibrosis, severe acute respiratory syndrome, extracorporeal membrane oxygenation, exposure to irritant gasses, thermal injury, smoke inhalation, SARS, anthrax, radiation exposure, chemicals or toxic substances, and infection.

Also disclosed is a method of protecting against or treating multiple organ failure following a hemorrhagic bleeding event comprising administering an effective amount of the δV1.1 PKC-Tat peptide.

In another aspect of the invention, a method to identify compounds which modulate δPKC activity is provided. An exemplary method entails providing cells which express δPKC, incubating the cells in the presence and absence of the test compound, and assessing the cells for alterations in said δPKC activity which occur in the presence, but not the absence, of said compound. δPKC activities which can be assessed in accordance with the foregoing method include, for example, recruitment of neutrophils, activation of ERK1/2, inhibition of caspase 3, NFκB activation, and superoxide anion generation.

BRIEF DESCRIPTION OF THE DRAWINGS

FIG. 2. (A) Primary sequence of rat δPKC (SEQ ID NO: 6) and mouse θPKC (SEQ ID NO: 7) V1 domains. The bracketed areas designated as δV1.1 and δV1.2 indicate regions of difference between the two isozymes. δPKC has only ~10% identity to θPKC. (B) Amino acid sequence of δPKC region, SEQ ID NO: 1, and the HIV Tat amino acid sequence, SEQ ID NO: 2, used in constructing the δV1.1 PKC-Tat peptide. (C) Human amino acid sequence of human PKC peptides useful in the present invention (SEQ ID NO: 3).

FIG. 7. 2CLP Activates NFκB in Rat Lungs. (A) NFKB DNA-binding activity in nuclear extracts prepared from lung tissue from Untreated controls (U) or from animals 48 hr post 2CLP. cc=cold competition with unlabeled oligonucleotide and ss=supershift. (B) p65 NFκB translocation to the nucleus. Lung tissue nuclear extracts were prepared from untreated controls or animals 48 hr after 2CLP and probed for the presence of p65 NFKB by Western blotting. (Representative EMSA and Western blot from n=3).

FIG. 21. (A) Targeted inhibition of δ-PKC activity will prevent proinflammatory signaling events in the lung. (B) Targeted inhibition of δ-PKC activity in the lung will prevent neutrophil activation. (C) Targeted inhibition of δ-PKC activity in the lung will prevent tissue injury and ARDS.

DETAILED DESCRIPTION OF THE INVENTION

Inhibition of neutrophil migration and inflammation is regarded as an important therapy for inflammatory disease. However, no suitable therapy currently exists for a stable anti-inflammatory effect. A greater therapeutic effect could be obtained if anti-inflammatory approaches can be used to deliver an inhibitor of neutrophil influx into the lung since activation and recruitment of neutrophils is an important factor in the development of ALI and ARDS.

Proinflammatory cytokines such as TNF are important regulators of neutrophil function during the inflammatory response through activation of proinflammatory signaling and suppression of neutrophil apoptosis (Kilpatrick, L. et al. (2002) Am. J. Physiol. Cell Physiol. 283:C48-C57; Dunican, A. et al. (2000) Shock 14:284-288). Neutrophils possess two TNF receptors, a 55-60 kDa (TNFR-1) and a 75-80 kDa (TNFR-2) receptor; proinflammatory and antiapoptotic signaling is regulated principally by TNFR-1 (Schall, T. et al. (1990) Cell 61:361-370). TNF can activate multiple signaling pathways; however, whether TNF signals for cell survival or apoptosis is dependent on both cell type and cellular environment.

The PKC family of serine/threonine kinases is composed of at least ten isozymes with distinctive means of regulation and tissue distribution (Tanaka, C. et al. (1994) Annu. Rev. Neurosci. 17:551-567). Five isozymes are known to be present in human neutrophils, yet the exact functional roles of these different isozymes in neutrophils remains to be specified (Karlsson A. et al (2002) antioxid. Redox Signal. 4:49-60). δPKC is a member of the PKC subfamily that is activated by diacylglycerol but not calcium. δPKC has been identified as a critical regulator of TNF signaling in neutrophils (Kilpatrick, L. et al. (2000) Amer. J. Physiol. 279:C2011-C2018; Kilpatrick, L. et al. (2002) Amer. J. Physiol. Cell Physiol. 283:C48-C59; Kilpatrick, L. et al. Am J Physiol Cell Physiol (2004) 287, C633-42) Kilpatrick, L. et al. J. Leuk. Biol. (2006) 80:1512-1521. δ-PKC is required for TNF-mediated inhibition of constitutive apoptosis and activation of NFκB in neutrophils through phosphorylation of TNFR-1 and assembly of the anti-apoptotic TNFR-1-TRADD-TRAF2-RIP signaling complex.

Cooperative signaling between TNF and β-integrins modifies the phosphorylation pattern of δPKC, and altered phosphorylation then targets δPKC to cellular locations and substrates that are crucial to TNF anti-apoptotic and proinflammatory responses. δPKC mediates TNF anti-apoptotic signaling through inhibition of caspase 3 (Kilpatrick, L. et al. (2002) Amer. J. Physiol. Cell Physiol. 283:C48-C59).

Figure 1:
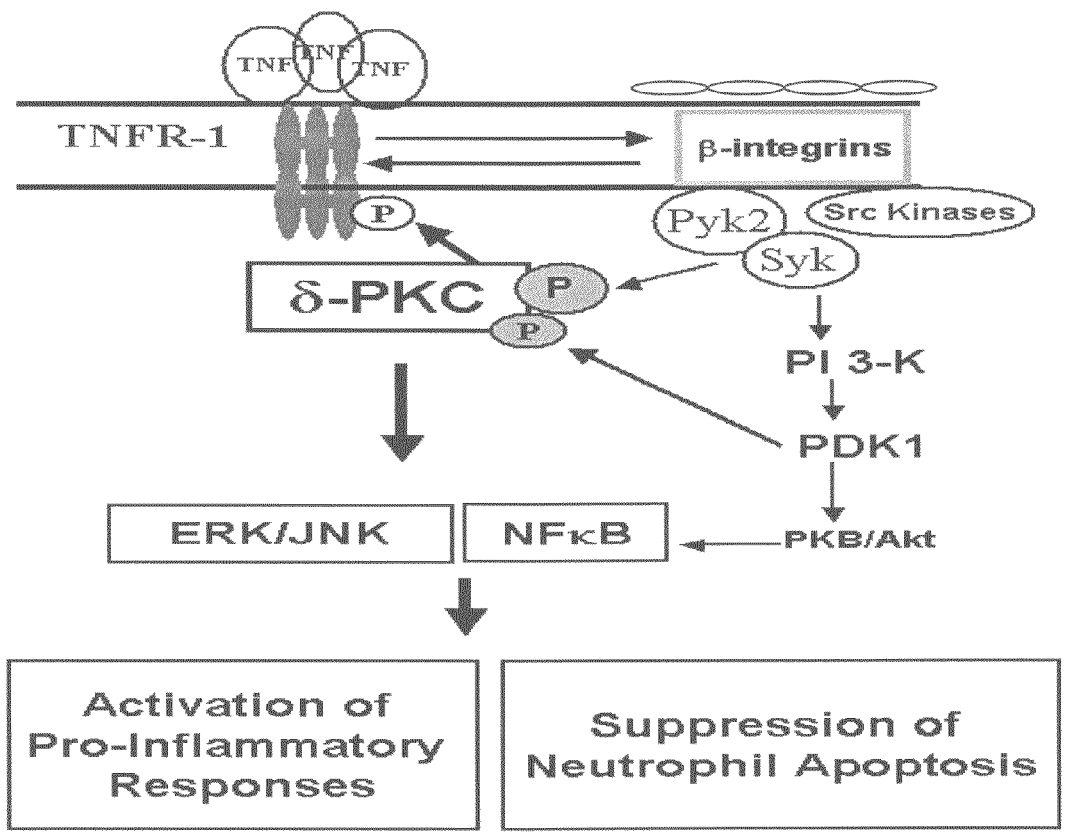
FIG. 1. Schematic diagram which illustrating hypothetical model of regulation of TNF signaling by δPKC in adherent neutrophils.

FIG. 1 is a schematic diagram which depicts δPKC as a critical regulator of neutrophil activity in response to TNF. Neutrophil adherence and ligation of β2-integrins activates outside-in signaling which significantly regulates the assembly of the TNFR-1 signaling complex through recruitment of unique effector proteins required for assembly of signaling pathways that mediate anti-apoptotic and pro-inflammatory signaling. These signaling pathways include NFκB, ERK, and JNK, but not p38 MAPK. δPKC is an important mechanistic link between TNF and β2-integrin signaling since δPKC activity is regulated by phosphorylation. Cooperative signaling between TNF and β2-integrins activates tyrosine kinases and PI-3-kinase. These kinases modify the phosphorylation pattern of δPKC and its subsequent activity and substrate specificity. PI-3-kinase also contributes to δPKC regulation through PDK-1 mediated phosphorylation of δPKC. These post-translational modifications of δPKC promote recruitment of δPKC to TNFR-1 receptor. δPKC then phosphorylates TNFR-1 on serine residues. Phosphorylation of TNFR-1 produces conformational changes that promote association of effectors that are necessary elements for the assembly and activation of anti-apoptotic and pro-inflammatory signaling.

In vivo and in vitro studies have demonstrated that δPKC has an important role in controlling both anti-apoptotic signaling and pro-inflammatory events in the neutrophil. In vitro studies using a dominant negative δPKC peptide demonstrated a role for δPKC in cytokine-mediated inhibition of constitutive neutrophil apoptosis and caspase activity (Kilpatrick, L. et al. (2002) Amer. J. Physiol: Cell Physiol. 283: C48-C59). δPKC has been shown to also be required for activation of the MAP kinase ERK and the transcription factor NFκB (Amer. J. Physiol.: Cell Physiol. (2002) 283:C48-C59; Amer. J. Physiol.: Cell Physiol (2004) 287:C633-C642; J. Biol. Chem. (2001) 276:19746-52, J. Leuk. Biol. (2006) 80: 1512-1521). δPKC also has a role in the regulation of neutrophil oxygen radical production and release of matrix metalloproteinase-9 (J. Leuk. Biol. (2006) 79:214-222; Molecular Cell (2003) 11:35-47). In δ-PKC null mice, neutrophil function is significantly altered (Chou, W. et al. (2004) J. of Clin. Invest. 114: 49-56). Neutrophils isolated from δ-PKC null mice demonstrated reduced adhesion and migration as compared to wild type littermates. Furthermore, oxygen radical production and release of granule contents were also significantly reduced in δPKC null neutrophils. In vivo, the absence of δPKC was associated with reduced infiltration of peripheral neutrophils into the infarcted tissue following transient ischemia. δPKC is also an important regulator of the adhesion molecule VCAM-1 expression on lung epithelial cells (Amer. J. Physiol. Lung Cell Mol Physiol. (2005) 288: L307-16). VCAM-1 interacts with its ligand β1-integrin on neutrophils and is crucial for mediating neutrophil adhesion to airway epithelium and infiltration into the lung. Systemic inhibition of δ-PKC resulted in reduced neutrophil influx into the lung airway following administration of pro-inflammatory mediators (LPS or TNF). In summary, in vivo and in vitro studies have demonstrated that δPKC has a significant role in the regulation of neutrophil recruitment to the lung, the activation of neutrophils in the lung compartment, and control of the lifespan of the neutrophil.

A δPKC antagonist peptide, δV1.1 PKC–Tat, has been described by Mochly-Rosen (U.S. Pat. No. 6,855,693) and preclinical studies have demonstrated that this inhibitory peptide, when used in conjunction with an activator of the protein kinase C, isotype epsilon (ε-PKC), reduces ischemia-reperfusion injury and decreases coronary artery disease induced by prolonged ischemia (Chen, L. et al. (2001) PNAS 98:11114-11119). Here, a novel composition and application of the δV1.1 PKC–Tat peptide can be utilized for the prevention and treatment of ALI and ARDS following trauma, hemorrhage, massive blood transfusion, thermal injury or infection to attenuate neutrophil activation and prevent neutrophil-mediated lung injury in patients.

Thus, the present invention relates to the use of δPKC inhibitors (δV1.1 PKC–Tat peptides) as anti-inflammatory agents for the treatment of inflammatory disease. In a preferred embodiment localized, aerosolized administration of the δV1.1 PKC–Tat inhibitor at the site of inflammation in the lung provides a higher effective dose at the site of inflammation. Localized administration of the inhibitor directly to the lung of the patient avoids systemic exposure to the peptide which may result in undesirable secondary side effects. Another advantage of localized aerosolized delivery is that this approach enables administration of lower doses of inhibitor which avoids the inefficient targeting of the δ-PKC inhibitor associated with systemic administration due to clearance by the liver or incomplete absorption in the intestine from oral administration. The compositions and methods are also advantageous in that they provide non-steroidal agents that are effective at decreasing inflammation in an inflammatory lung disease, which can thereby alleviate signs or symptoms associated with ALI or ARDS. Administration of the compositions described herein can decrease pulmonary neutrophil activation by at least 2-fold, by at least 3-fold, and preferably by at least 5-fold relative to untreated controls, thereby preventing further injury and inflammation to the lung.

Aerosolization provides an excellent method for delivering δPKC inhibitors such as the δV1.1 PKC–Tat peptide described herein. Utilizing this approach, δPKC inhibitors can be delivered directly in the local environment of the inflammation or infection as an aerosol, thereby targeting adherent neutrophils and preventing further injury. Simultaneously, a membrane permeant peptide sequence in the HIV Tat gene product is coupled to the δPKC inhibitor. The protein transduction domain of the HIV Tat protein can mediate the transduction of biologically active compounds into target cells as described in Science ((1999) 285:1569-1572)).

In the present invention, δPKC is selectively inhibited using a δV1.1 PKC–Tat peptide antagonist. In particular, this construct consists of a peptide derived from the first unique region (V1) of δPKC (SFNSYELGSL: amino acids 8-17 of δPKC, SEQ ID NO: 1), coupled to a membrane permeant peptide sequence in the HIV Tat gene product (YGRKKRRQRRR: amino acids 47-57 of Tat, SEQ ID NO: 2), according to the method of Mochly-Rosen et al. (Proc. Natl. Acad. Sci. (2001) 98, 11114-9). In another embodiment, the sequence from human δPKC may be used which has the sequence of SEQ ID NO: 3 which can be used in the treatment of human patients. See FIG. 2C. The δPKC peptide is cross-linked by an N-terminal Cys-Cys bond to the Tat peptide. This δV1.1 PKC–Tat peptide antagonist has been shown to selectively prevent the translocation and activation of δPKC and does not affect the activity of other members of the PKC family of protein kinases.

Tat peptide mediated transduction of proteins or peptides into cells is concentration dependent and receptor, transporter, and endocytotic-independent. Studies have shown that Tat-linked peptides are taken up into mouse lung after intratracheal instillation (J. Controlled Release (2005) 109:299-316) and Tat-linked peptides can inhibit inflammatory and apoptotic pathways in vivo as described in (J. Immunology, (2003) 171: 4379-4384; J. Exp. Med. (2003) 198:1573-82; J. Immunology (2006) 176:5471-77).

In animal studies, δV1.1 PKC–Tat exhibits a very strong inhibition of neutrophil activation at sites of inflammation, consistent with previous reports of reducing ischemia-reperfusion injury and coronary artery disease induced by ischemia (Chou, W. et al. (2004) J. Clin. Invest. 114:49-56).

Based on the foregoing observations, δPKC inhibitors and delivery methods are provided as a novel therapy to treat ALI and ARDS following trauma, hemorrhage, burn or infection. Exemplary methods entail delivering δPKC inhibitor peptides into patients with neutrophil-mediated lung injury. The compositions of the invention can be directly delivered to the lung, as opposed to previous studies which have not investigated delivery to the pulmonary system.

Thus, a new approach for treating ALI and ARDS is described herein. The peptides of the invention may be used alone or combined with other anti-inflammatory agents or genes encoding anti-inflammatory proteins to augment the anti-inflammatory efficacy of the peptides.

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1997) (hereinafter "Ausubel et al.") are used.

I. Definitions:

The following definitions are provided to facilitate an understanding of the present invention:

As used herein, the term "PKC" refers to protein kinase C. The invention is focused on the activity of PKC, isotype delta (δ).

As used herein, the terms "δPKC inhibitor"; "δV1.1 PKC–Tat"; "δPKC–TAT inhibitor"; "dominant negative δ-PKC TAT peptide"; and the like (i.e., "cell permeant DN δ-PKC TAT peptide", are all intended to refer to a peptide that inhibits or reduces the activity of protein kinase C, isotype delta. δPKC, to which inhibitors of the invention are directed, is the protein present in eukaryotes, for example, δPKC is present in mammals, and in particular the δPKC is present in primates, including humans.

An "inflammatory lung disease" refers to a disease associated with an inflammatory or immune response in the lung. Inflammatory lung diseases include, for example, ALI, ARDS, asthma, emphysema, chronic bronchitis, cystic fibrosis, infection, physical trauma, hemorrhage and interstitial lung disease such as interstitial pneumonitis, idiopathic fibrosis and interstitial fibrosis.

As used herein, the term "treating an inflammatory lung disease" is intended to refer to the alleviation of a sign or symptom of the inflammatory lung disease. Treating an inflammatory lung disease is intended to encompass a reduction in the onset or magnitude of a sign or symptom of an inflammatory lung disease, such as the recruitment of neutrophils.

The term "aerosol formulation" refers to a pharmaceutical composition suitable for administration through the respiratory system or nasal passages. Examples of aerosol formulations are described below. Similarly, the term "aerosol administration" is intended to refer to a mode of administering an aerosol formulation to the respiratory system or nasal passages.

The invention provides a composition of matter comprising an aerosol formulation of the δPKC inhibitor where the δPKC inhibitor is present at a concentration ranging from 0.001 mg to 3500 mg. In particular, the invention provides a composition of matter comprising a δPKC inhibitor that is a peptide. Peptides of the invention can be functional fragments of proteins.

"Peptide" and "polypeptide" are used interchangeably herein and refer to a compound made up of a chain of amino acid residues linked by peptide bonds. The sequence for peptides is given in the order from the amino terminus to the carboxyl terminus. A peptide or peptide fragment is "derived from" a parent peptide or polypeptide if it has the amino acid sequence that is identical or homologous to the amino acid sequence of the parent peptide or polypeptide.

The phrase "Nucleic acid" or "nucleic acid molecule" or "polynucleotide" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

"Foreign cDNA" or "exogenous nucleic acid" as used herein refers to any nucleic acid not native to the adenoviral vector. The exogenous nucleic acid encodes a peptide that exerts a biological effect in a host cell such as, for example, a peptide that is associated with or treats a biological disorder or phenomenon. The exogenous nucleic acid can be obtained from any source, e.g., isolated from nature, synthetically generated, isolated from a genetically engineered organism, and the like.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The terms "transform", "transfect", "transduce", shall refer to any method or means by which a nucleic acid is introduced into a cell or host organism and may be used interchangeably to convey the same meaning. Such methods include, but are not limited to, Tat-peptide-tethering, transfection, electroporation, microinjection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "substantially pure" refers to a preparation comprising at least 50-60% by weight of a given material (e.g., peptide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

The term "functional" as used herein implies that the nucleic or amino acid sequence is functional for the recited assay or purpose.

The phrase "consisting essentially of" when referring to a particular amino acid means a sequence having the properties of a given SEQ ID NO. For example, when used in reference to an amino acid sequence, the phrase includes the sequence per se and molecular modifications that would not affect the basic and novel characteristics of the sequence.

The term "nanoparticle" refers to a particle having a size measured on the nanometer scale. As used herein, the "nanoparticle" refers to a particle having a matrix-type structure with a size of less than about 1,000 nanometers. When the nanoparticle includes a bioactive component, the bioactive component is entangled or embedded in the matrix-type structure of the nanoparticle. Nanoparticles include particles capable of containing a therapeutic agent that is to be released within a mammalian body, including specialized forms such as nanospheres, whether natural or artificial.

The term "tag," "tag sequence" or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography. Chemical tag moieties include such molecules as biotin, which may be added to either nucleic acids or proteins and facilitates isolation or detection by interaction with avidin reagents and the like. Numerous other tag moieties are known to, and can be envisioned by the skilled artisan, and are contemplated to be within the scope of this definition.

As disclosed herein, δPKC inhibitors are effective at reducing a sign or symptom of inflammation and thus are useful for the treatment of inflammatory disorders. The compositions of the invention are effective at inhibiting the adherence of neutrophils and the infiltration of inflammatory cells, such as neutrophils, into the lung in an animal model of inflammatory disease, and in human subjects.

The methods of the invention are particularly useful for treating inflammatory lung disease, including, for example, ALI, ARDS, asthma, emphysema, chronic bronchitis, cystic fibrosis, infection, physical trauma, hemorrhage and interstitial lung disease such as interstitial pneumonitis, idiopathic fibrosis and interstitial fibrosis. ALI occurs when an insult to the lung causes an acute inflammatory reaction which results in respiratory distress, hypoxemia and diffuse alveolar infiltrates, and can ultimately lead to respiratory failure. ALI can occur with a variety of pulmonary insults, including, for example, sepsis and trauma. The extent of ALI depends, for example, on the magnitude of initial damage, repeated insults such as persistent septicemia or retained necrotic and inflamed tissue, and added insults from treatment including barotrauma, hyperoxia and nosocomial infection.

ARDS is a form of acute lung injury often seen in previously healthy patients. ARDS is characterized by rapid respiratory rates, a sensation of profound shortness of breath, severe hypoxemia not responsive to supplemental oxygen, and widespread pulmonary infiltrates by cardiovascular disease or volume overload. ARDS tends to follow a diverse array of systemic and pulmonary insults, although the majority of ARDS is associated with systemic or pulmonary infection, severe trauma, or aspirating gastric contents. The crucial stimulus to the development of ARDS is an inflammatory response to distant or local tissue injury. Disorders associated with ARDS include aspiration of gastric contents, fresh and salt water and hydrocarbons; central nervous system trauma, anoxia, seizures or increased intracranial pressure; drug overdose or reactions; hematologic alterations; infection, including sepsis, pneumonia and tuberculosis; inhalation of toxins such as oxygen, smoke or corrosive chemicals; metabolic disorders such as pancreatitis; shock; and trauma such as fat emboli, lung contusion, severe nonthoracic trauma and cardiopulmonary bypass.

During lung injury, an inflammatory response triggers neutrophil adhesion to endothelium and transmigration to tissue and subsequent neutrophil-mediated endothelial and tissue injury.

II. Pharmaceutical Compositions:

Methods of the invention directed to treating an inflammatory lung disease, for example, ALI, ARDS, and conditions related to trauma, involve the administration of a δV1.1 PKC–Tat inhibitor in a pharmaceutical composition. A δV1.1 PKC–Tat inhibitor is administered to an individual as a pharmaceutical composition comprising a δV1.1 PKC–Tat inhibitor and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters.

A pharmaceutically acceptable carrier can contain physiologically acceptable compounds that act, for example, to stabilize the δV1.1 PKC–Tat inhibitor or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the δV1.1 PKC–Tat inhibitor and on the particular physico-chemical characteristics of the specific δV1.1 PKC–Tat.

One skilled in the art appreciates that a pharmaceutical composition comprising a δV1.1 PKC–Tat inhibitor can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intratracheally (i.t), intra-articularly or by passive or facilitated absorption through the skin using, for example, a skin patch or transdermal iontophoresis, respectively. Thus, a δV1.1 PKC–Tat inhibitor can be administered systemically by injection, intubation, or orally, or can be administered locally by topical application, the latter of which can be passive, for example, by direct application of an ointment or powder, or active, for example, and most preferably, using a nasal spray or inhalant.

Administration of a δV1.1 PKC–Tat inhibitor by inhalation is a particularly preferred means of treating an individual having an inflammatory lung disease. One skilled in the art would recognize that a δV1.1 PKC–Tat inhibitor can be suspended or dissolved in an appropriate pharmaceutically acceptable carrier and administered, for example, directly into the lungs using a nasal spray or inhalant.

A pharmaceutical composition comprising a δV1.1 PKC–Tat inhibitor can be administered as an aerosol formulation which contains the inhibitor in dissolved, suspended or emulsified form in a propellant or a mixture of solvent and propellant. The aerosolized formulation is then administered through the respiratory system or nasal passages.

An aerosol formulation used for nasal administration is generally an aqueous solution designed to be administered to the nasal passages in drops or sprays. Nasal solutions are generally prepared to be similar to nasal secretions and are generally isotonic and slightly buffered to maintain a pH of about 5.5 to about 6.5, although pH values outside of this range can additionally be used. Antimicrobial agents or preservatives can also be included in the formulation.

An aerosol formulation used for inhalations and inhalants is designed so that the δV1.1 PKC–Tat inhibitor is carried into the respiratory tree of the patient administered by the nasal or oral respiratory route. Inhalation solutions can be administered, for example, by a nebulizer. Inhalations or insufflations, comprising finely powdered or liquid drugs, are delivered to the respiratory system as a pharmaceutical aerosol of a solution or suspension of the drug in a propellant.

An aerosol formulation generally contains a propellant to aid in disbursement of the δV1.1 PKC–Tat inhibitor. Propellants can be liquefied gases, including halocarbons, for example, fluorocarbons such as fluorinated chlorinated hydrocarbons, hydrochlorofluorocarbons, and hydrochlorocarbons as well as hydrocarbons and hydrocarbon ethers (Reminaton's Pharmaceutical Sciences 18th ed., Gennaro, A. R., ed., Mack Publishing Company, Easton, Pa. (1990)).

Halocarbon propellants useful in the invention include fluorocarbon propellants in which all hydrogens are replaced with fluorine, hydrogen-containing fluorocarbon propellants, and hydrogen-containing chlorofluorocarbon propellants. Halocarbon propellants are described in Johnson, U.S. Pat. No. 5,376,359, and Purewal et al., U.S. Pat. No. 5,776,434.

Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as numerous other ethers.

The δV1.1 PKC-Tat inhibitor can also be dispensed with a compressed gas. The compressed gas is generally an inert gas such as carbon dioxide, nitrous oxide or nitrogen.

An aerosol formulation of the invention can also contain more than one propellant. For example, the aerosol formulation can contain more than one propellant from the same class such as two or more fluorocarbons. An aerosol formulation can also contain more than one propellant from different classes. An aerosol formulation can contain any combination of two or more propellants from different classes, for example, a fluorohydrocarbon and a hydrocarbon.

Effective aerosol formulations can also include other components, for example, ethanol, isopropanol, propylene glycol, as well as surfactants or other components such as oils and detergents (Remington's Pharmaceutical Sciences, 1990; Purewal et al., U.S. Pat. No. 5,776,434). These aerosol components can serve to stabilize the formulation and lubricate valve components.

The aerosol formulation can be packaged under pressure and can be formulated as an aerosol using solutions, suspensions, emulsions, powders and semisolid preparations. A solution aerosol consists of a solution of an active ingredient such as a δV1.1 PKC-Tat inhibitor in pure propellant or as a mixture of propellant and solvent. The solvent is used to dissolve the active ingredient and/or retard the evaporation of the propellant. Solvents useful in the invention include, for example, water, ethanol and glycols. A solution aerosol contains the active ingredient δV1.1 PKC-Tat inhibitor and a propellant and can include any combination of solvents and preservatives or antioxidants.

An aerosol formulation can also be a dispersion or suspension. A suspension aerosol formulation will generally contain a suspension of a δV1.1 PKC-Tat inhibitor and a dispersing agent. Dispersing agents useful in the invention include, for example, sorbitan trioleate, oleyl alcohol, oleic acid, lecithin and corn oil. A suspension aerosol formulation can also include lubricants and other aerosol components.

An aerosol formulation can similarly be formulated as an emulsion. An emulsion can include, for example, an alcohol such as ethanol, a surfactant, water and propellant, as well as the active ingredient δV1.1 PKC-Tat inhibitor. The surfactant can be nonionic, anionic or cationic. One example of an emulsion can include, for example, ethanol, surfactant, water and propellant. Another example of an emulsion can include, for example, vegetable oil, glyceryl monostearate and propane.

An aerosol formulation containing a δV1.1 PKC-Tat inhibitor will generally have a minimum of 90% of the particles in inhalation products between about 0.5 and about 10 μm to maximize delivery and deposition of the δV1.1 PKC-Tat inhibitor to respiratory fluids. In particular, the particle size can be from about 3 to about 6 μm.

A pharmaceutical composition comprising a δV1.1 PKC-Tat inhibitor also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer. Liposome-based methods are useful since in certain circumstances peptides can be damaged (i.e., structural damage) during preparation with carriers. Thus, for certain applications of particular aspects of the instant invention, it may be preferable to utilize liposome-based delivery. For example, suitable methods are described in Torchilin (Advanced Drug Delivery Reviews (2008) 60:548-558); Cryan et al. (Advanced Drug Delivery Reviews (2007) 59:1133-1151); Kleemann et al. (J. Controlled Release (2005) 109:299-316; and Cryan et al. (Molecular Pharmaceutics (2006) 3:104-112).

Nanoparticles can also be used to deliver the inhibitory δPKC-Tat peptide, particularly to the pulmonary system. As one of skill in the art will appreciate, a nanoparticle in accordance with the methods and compositions of the present invention can be composed of a variety of injectable biodegradable polymers. Nanoparticles are said to be biodegradable if the polymer of the nanoparticle dissolves or degrades within a period that is acceptable in the desired application (usually in vivo therapy), usually less than five years, and desirably less than one year, upon exposure to a physiological solution of pH 6-8 having a temperature of between 25° C. and 37° C. As such, a nanoparticle for use in accordance with the methods and compositions of the present invention can be composed of homopolymers or copolymers prepared from monomers of polymers, wherein the copolymer can be of diblock, triblock, or multiblock structure as described in U.S. Patent Application 20060067925. Suitable polymers include, but are not limited to, poly(lactide-co-glycolides), poly(lactic acid), poly(alkylene glycol), polybutylcyanoacrylate, poly(methylmethacrylate-co-methacrylic acid), poly-allylamine, polyanhydride, polyhydroxybutyric acid, or polyorthoesters and the like. Particular combinations and ratios of polymers are well-known to the skilled artisan and any suitable combination can be used in the nanoparticle formulations of the present invention. Suitable formulations for use with the inhibitory peptide described herein are disclosed in international application PCT/US08/069519, which is incorporated by reference. Generally, the resulting nanoparticle typically ranges in size from between 1 nm and 1000 nm, or more desirably between 1 nm and 100 nm.

In order to treat an individual having an inflammatory lung disease to alleviate a sign or symptom of the disease, a δV1.1 PKC-Tat inhibitor should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of a δV1.1 PKC-Tat inhibitor required to obtain an effective dose in a subject depends on many factors, including the particular inflammatory lung disease being treated, the age, weight and general health of the subject, as well as the route of administration and the number of treatments to be administered. In view of these factors, the skilled artisan would adjust the particular dose so as to obtain an effective dose for treating an individual having an inflammatory lung disease.

The effective dose of a δV1.1 PKC-Tat inhibitor will depend on the mode of administration, and the weight of the individual being treated. The dosages described herein are generally those for an average adult. The dose will generally range from about 0.001 mg to about 3500 mg. Unlike the use of δV1.1 PKC-Tat inhibitors for the treatment of ischemia, the present invention is directed to methods of treating inflammation in the lung, which can be treated as an acute response. Therefore, the δV1.1 PKC-Tat inhibitors of the invention can be administered at high doses relative to those given for ischemia and reperfusion. The dose will generally be at least about 10 mg per day, at least about 100 mg per day, at least about 200 mg per day, at least about 250 mg per day, at least about 300 mg per day, at least about 400 mg per day, or at least about 500 mg per day, and can be at least about 1000 mg per day. When administering high doses of a δV1.1 PKC-Tat inhibitor, one skilled in the art can monitor for any possible adverse side effects. Methods of monitoring adverse side effects of a δV1.1 PKC-Tat inhibitor are known in the art. One of skilled in the art can monitor for any adverse side effects and, if necessary, adjust the dosage to minimize adverse side effects while optimizing the effectiveness of treating an inflammatory lung disease.

For administration in an aerosol formulation, the dose of δV1.1 PKC-Tat inhibitor can generally be lower than the dose used for systemic administration. For example, a δV1.1 PKC-Tat inhibitor can be administered at a dose lower than about 10 mg per day, generally lower than about 1 mg per day, and in particular lower than about 0.1 mg day. The δV1.1 PKC-Tat inhibitor can be administered at a dose of less than 0.1 mg per day, for example, about 0.09 mg per day or less, about 0.08 mg per day or less, about 0.07 mg per day or less, about 0.06 mg per day or less, about 0.05 mg per day or less, about 0.04 mg per day or less, about 0.03 mg per day or less, about 0.02 mg per day or less, or about 0.01 mg per day or less.

The concentration of a δV1.1 PKC-Tat inhibitor in a particular formulation will depend on the mode and frequency of administration. A given daily dosage can be administered in a single dose or in multiple doses so long as the δV1.1 PKC-Tat inhibitor concentration in the formulation results in the desired daily dosage. For example, a given formulation can contain a δV1.1 PKC-Tat inhibitor at a concentration of about 0.09 mg, about 0.08 mg, about 0.07 mg, about 0.06 mg, about 0.05 mg, about 0.04 mg, about 0.03 mg, about 0.02 mg or about 0.01 mg. A given formulation can also contain a δV1.1 PKC-Tat inhibitor at a concentration of about 0.005 mg, about 0.002 mg or about 0.001 mg. One skilled in the art can adjust the amount of δV1.1 PKC-Tat inhibitor in the formulation to allow administration of a single dose or in multiple doses that provide the desired concentration of δV1.1 PKC-Tat inhibitor over a given period of time. For example, the formulation can be adjusted to allow administration of a single dose or multiple doses that provides less than 0.1 mg per day of a δPKC inhibitor.

In an individual suffering from an inflammatory lung disease, in particular a more severe form of the disease, administration of a δV1.1 PKC-Tat inhibitor can be particularly useful when administered in combination, for example, with a conventional agent for treating such a disease. The skilled artisan would administer a δV1.1 PKC-Tat inhibitor, alone or in combination with a second agent, based on the clinical signs and symptoms exhibited by the individual and would monitor the effectiveness of such treatment using routine methods such as pulmonary function determination, radiologic, immunologic or, where indicated, histopathologic methods.

A δV1.1 PKC-Tat inhibitor can be administered in combination with steroidal anti-inflammatory agents including corticosteroids, for example, dexamethasone, beclomethasone, fluticasone, triamcinolone and budesonide. A δV1.1 PKC-Tat inhibitor can also be administered in combination with non-steroidal anti-inflammatory agents such as aspirin (acetylsalicylic acid), indomethacin, ibuprofen, naproxen, diclofenac, sulindac, oxaprozin, diflunisal, bromfenac, piroxicam, etodolac and fenoprofen. When a δV1.1 PKC-Tat inhibitor is used with another anti-inflammatory agent, the δV1.1 PKC-Tat inhibitor can generally be administered at a lower dosage. For example, a δV1.1 PKC-Tat inhibitor can be administered at a dose of less than 0.1 mg per day in combination with another anti-inflammatory agent.

When a δV1.1 PKC-Tat inhibitor is administered in combination with one or more other anti-inflammatory agent, the δV1.1 PKC-Tat inhibitor and other anti-inflammatory agent can be co-administered in the same formulation. Alternatively, the δV1.1 PKC-Tat inhibitor and other anti-inflammatory agent can be administered simultaneously in separate formulations. In addition, the δV1.1 PKC-Tat inhibitor can be administered in separate formulations, where the separate formulations are not administered simultaneously but are administered during the same period of treatment, for example, during a daily or weekly period of treatment.

Administration of the pharmaceutical preparation is preferably in a "prophylactically effective amount" or a "therapeutically effective amount" (as the case may be, although prophylaxis may be considered therapy), this being sufficient to show benefit to the individual. This amount prevents, alleviates, abates, or otherwise reduces the severity of symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art. As mentioned previously, a preferred embodiment of the invention comprises aerosolized delivery of the δV1.1 PKC-Tat peptide to the lungs of a patient in need thereof. The δV1.1 PKC-Tat peptide described herein can also be injected intra-peritoneally (i.p.), intravenously (i.v.), or intratracheally (i.t.). Formulation, dosages and treatment schedules have also been described hereinabove.

The following materials and methods are provided to facilitate practice of the present invention:

Construction of δPKC Inhibitor Peptide:

The peptide may be chemically synthesized or produced recombinantly in a host cell using an expression vector containing the polynucleotide fragment encoding said inhibitory peptide, where the polynucleotide fragment is operably linked to a promoter capable of expressing mRNA from the fragment in a host cell. δV1-1 PKC-Tat was commercially synthesized at Mimotopes (Melbourne, Australia). δPKC (amino acids 8-17) peptide, SEQ ID NO: 1, was conjugated to the HIV Tat (amino acids 47-57) peptide fragment, SEQ ID NO: 2, via a cysteine-cysteine bond at their amino termini and purified by HPLC. As mentioned previously, SEQ ID NO: 3 from human δPKC may also be utilized in connection with the HIV Tat peptide sequence for use in human subjects.

Reagents:

Recombinant human TNFα and mouse monoclonal anti-human TNFR-2 and TNFR-1 blocking antibodies were obtained from R&D Systems (Minneapolis, Minn.). The mouse monoclonal anti-human CD120a (TNFR-1) was obtained from Cell Sciences (Norwood, Mass.). Polyclonal rabbit antiphosphoserine and membrane blocking solution were obtained from Zymed Laboratories (San Francisco, Calif.). Rabbit polyclonal antibodies against Thr202/Tyr204-phosphorylated ERK1/2, ERK1/2, Thr180/Tyr182-phosphorylated p38 MAPK, and p38 MAPK were purchased from Cell Signaling Technology (Beverly, Mass.). LY294002 was obtained from Calbiochem (San Diego, Calif.). Polyclonal rabbit anti-human-δ-PKC, anti-βII-PKC, α-PKC and ζ-PKC, goat anti-human TNFR-1, goat anti-mouse IgG-HRP, and goat anti-rabbit IgG-HRP were obtained from Santa Cruz Biotechnology (Santa Cruz, Calif.). The MAPK inhibitors, PD098059, U0126, SB203580 were obtained from BioMol (Plymouth Meeting, Pa.). EGTA, goat anti-mouse IgG agarose, Na-orthovanadate, 4-(2-aminoethyl)-benzenesulfonyl fluoride, leupeptin, protease inhibitor cocktail, and phosphatase inhibitor cocktail were obtained from Sigma (St. Louis, Mo.). SuperSignal ULTRA chemiluminescence substrate, dimethylpimelimidate (DMP), and bicinchoninic acid (BCA) reagents were obtained from Pierce (Rockford, Ill.).

Neutrophil Culture:

Neutrophils were isolated from heparinized venous blood (10 U/ml) obtained from adult donors following informed consent in accordance with Institutional Review Board protocols at the Children's Hospital of Philadelphia. Donors were healthy adults over the age of eighteen who were recruited from the Children's Hospital of Philadelphia community. The study population included both males and females and represented the ethnic population at Children's Hospital of Philadelphia. Standard isolation techniques were used employing Ficoll-Hypaque centrifugation, followed by dextran sedimentation and hypotonic lysis to remove residual erythrocytes. Cells were suspended in 10 mM HEPES buffer (pH 7.4). Neutrophil purity was greater than 96% as determined by morphology and Giemsa staining, and viability was greater than 98% as determined by trypan blue exclusion.

Neutrophil Transmigration:

As adapted from Am. J. Cell. Mol. Bio. (2009) 40:519, human pulmonary microvascular endothelial cells (PMVEC) monolayers were grown to confluency on transwell membranes coated with collagen as monitored by measuring transmonolayer resistance with an ohmmeter. PMVEC monolayers were pretreated with buffer, IL-1 (10 U/ml), or IL-1+ δ-PKC TAT inhibitory peptide (1 µM). The monolayers were washed and neutrophils ($2 \times 10^6$ cells/well) were added to the upper wells and allowed to migrate across the PMVEC monolayers for 3 hrs at 37° C. in 5% $CO_2$. Following incubation, the transwells were removed and neutrophils in the bottom wells were collected and counted.

HL-60 Cell Culture and δPKC siRNA:

Human promyelocytic HL60 leukemic cells were grown in suspension culture in RPMI 1640 medium supplemented with 2 mM L-glutamine, 1% nonessential amino acids, 1% MEM vitamin solution, 0.1% gentamicin, and 10% heatinactivated fetal bovine serum (FBS). HL60 cells were cultured at 37° C. in the presence of 1.3% DMSO for 4 days to initiate differentiation to a neutrophil-like phenotype (dHL60 cells) before treatment with siRNA. Cells were resuspended in Opti-MEM I reduced serum medium at a cell concentration of $25 \times 10^6$ cells/800 µl. Validated stealth RNAi (Invitrogen) was used to target δPKC (Target sequence 5'-CCACUACAU-CAAGAACCAUGAGUUU-3' (SEQ ID NO: 4)). siRNA with equivalent % GC nucleotide content was used as a control. Delivery of stealth siRNA (500 nM) was enhanced by electroporation at 270 V and 500 µFd, followed by culture in RPMI containing 10% heat inactivated FBS for 48 h. Levels of specific PKC isotypes were determined in cell lysates by immunoblotting with isotype-specific antibodies to α-PKC, β-PKC, δ-PKC, and ζ-PKC.

Measurement of ERK1/2 and p38 MAPK Phosphorylation:

For inhibitor experiments, neutrophils ($20 \times 10^6$ cells/well) were incubated with blocking antibodies against TNFR1 and TNFR2 or the PI 3-kinase inhibitor LY 294002 (10 µM) for 20 min before the addition of TNF. For experiments examining the role of δPKC, neutrophils were pretreated with buffer, δV1.1 PKC–Tat peptide (1 M), or Tat carrier peptide (1 µM) alone for 120 min at room temperature. After incubation with buffer or TNF (50 ng/ml) at 37° C. for varying time intervals, the cells were harvested and the cell lysates were prepared. The cells were lysed in lysis buffer containing 10 mM HEPES pH 7.4, 150 mM NaCl, 5 mM EDTA, 1 mM Na-orthovanadate, 20 µM 4-(2-aminoethyl)-benzenesulfonyl fluoride, 1% triton X-100, 5 g/ml leupeptin, Sigma phosphatase inhibitor cocktail, and Sigma protease inhibitor cocktail. The cell lysates were run on 4-12% SDS-PAGE gels at a protein concentration of 30 µg/lane. MAPK activation was determined by immunoblotting of cell lysates using phospho-specific antibodies for ERK1/2 (Thr202/Tyr204) and p38 MAPK (Thr180/Tyr182). Equal loading of specific MAPKs was confirmed by reprobing membranes using antibodies that recognize both phosphorylated and nonphosphorylated forms of the specific MAPK. MAPK activation was quantitated by densitometry analysis of Western blot analyses using the software SigmaProscan (Jandel/SPSS), and the results are expressed as means±SE (n=4) in arbitrary densitometry units (ADU).

Animal Experiments:

Sepsis models can be established by cecal ligation and double puncture of Sprague-Dawley rats. The δPKC inhibitor peptide of the invention may be administered into the trachea of the animals. Following the procedure, animals may be resuscitated and sacrificed at various time intervals at which time blood and tissue samples can be collected to for further testing related to neutrophil activation and lung injury.

Induction of Intra-Abdominal Sepsis in Animals and Intra-Tracheal Administration of δ-PKC TAT peptide:

Intra-abdominal sepsis was induced in rats by cecal ligation and double puncture (2CLP) as described previously (Weiss, Y. G., et al. (2001) Anesthesiology 95, 974-82; Weiss, Y. G., et al. (2002) J Clin Invest 110, 801-6; Weiss, Y. G., et al. (2007) Crit Care Med. 35:2128). Under sterile conditions and isoflurane anesthesia, male Sprague-Dawley rats (225-250 g) were subjected to cecal ligation and double puncture (2CLP) with an 18-gauge needle. For sham surgery, animals were subjected to sham laparotomy without cecal ligation or puncture. Following 2CLP or sham surgery, the abdominal incision was closed and a 0.5 cm incision was opened on the ventral surface of the neck. The muscles carefully separated, the trachea exposed, and a 24-gauge intravenous cannula was inserted into the trachea. The δ-PKC TAT peptide (e.g., 200 µg/kg) or PBS was administered 30 minutes post-injury (e.g., in a total volume of 200 µl delivered in two equal aliquots). After the procedure, animals were fluid resuscitated with 40 ml/kg sterile saline administered subcutaneously. Fluid resuscitation was repeated every 24 hours until sacrifice. In some cases, at 24-hrs post-surgery, animals were sacrificed and lung tissue, plasma and BAL fluid were collected. At the time of sacrifice, animals were anesthetized and BAL fluid (BALF) collected by instilling and withdrawing 1.5 ml of sterile PBS three times from the lungs via an intra-tracheal cannula as described previously (Weiss, Y. G., et al. (2001) Anesthesiology 95, 974-82).

Lung Permeability:

The effect of the δ-PKC TAT inhibitory peptide on capillary leak was assessed by determining total protein levels in BAL fluid from sham, 2CLP+PBS and 2CLP+δ-PKC TAT-treated rats.

Lung Histology:

The effect of 2CLP on lung histology was determined as described previously Weiss, Y. G., et al. (2001) Anesthesiology 95, 974-82; Weiss, Y. G., et al. (2002) J Clin Invest 110, 801-6). At the time of animal sacrifice, the animals were anesthetized and the lungs were inflated and fixed overnight in 10% neutral buffered formalin. Lung sections were coded and then stained with hematoxylin and eosin. Blinded sections were evaluated by an independent pathologist for alterations consistent with ARDS such as neutrophil infiltration, septal thickening, and protein and fluid accumulation in the interstitial and alveolar spaces.

The effect of 2CLP on rat lung NFκB activation was determined in nuclear extracts prepared from lung tissue as described by us previously (Weiss, Y. G., et al. (2007) Crit Care Med. 35:2128). Electrophoretic Mobility Shift Analysis (EMSA) of NF-κB DNA Binding Activity was performed using a $^{32}$P-labeled double-stranded DNA oligonucleotide containing a consensus-κB binding site (5'-TC-GAGAGATGGGGAATCCCCAGCC-3' (SEQ ID NO: 5). The labeled oligonucleotide was purified on a G-25 Sephadex column. Nuclear extracts containing 5 μg of protein were incubated with binding buffer (20 mM Hepes, (pH 7.9), 60 mM KCl, 2 mM EDTA, 5 mM MgCl2, 10% glycerol, 1 mM PMSF, 1 mM DTT, 0.1% NP-40), dIdC (1 μg/μl) for 20 min at room temperature. The labeled oligonucleotide was added to the reaction mixture for 20 min. Specificity for the binding site was determined by cold competition using a ten-fold excess of unlabeled oligonucleotide while supershift analysis with either anti-P65 or anti-P50 established the identity of the bound proteins. Complexes were visualized by autoradiography. Translocation of p65NFκB to the nucleus was determined by preparing nuclear extracts of lung tissue and probing for the presence of p65 NFκB by Western blotting.

Chemokine Measurements:

The levels of chemokines CINC-1 (Cytokine Induced Neutrophil Chemoattractant) (R & D Systems) and MIP-2 (BioSource) were measured by ELISA in BAL supernatants and plasma. Also, expression of the cytokines/chemokines CINC-1 and IL-6 levels was determined in lung tissue by Western blotting as described by us previously (Weiss, Y. G., et al. (2007) Crit Care Med. 35:2128). IL-6 was identified in whole lung extracts using a polyclonal rat anti-IL-6 (PeproTech, Rocky Hill, N.J.). CINC-1 was identified in whole lung extracts using a polyclonal goat anti CINC-1 (Santa Cruz Biotech Inc.).

Immunoprecipitation of TNFR-1:

Human neutrophils ($50 \times 10^6$ cells/condition) were pretreated with buffer, δ PKC–Tat peptide (1 uM), or Tat carrier peptide (1 uM) for 120 min at room temperature prior to the addition of TNF (50 ng/ml) or buffer for 5 min. The cells were lysed in immunoprecipitation (IP) buffer and vortexed for 20 min at 4° C. to solubilize the membrane fraction. The IP buffer consisted of 10 mM Hepes, pH 7.4, 150 mM NaCl, 5 mM EDTA, 1 mM Na-orthovanadate, 20 uM 4-(2-aminoethyl)-benzenesulfonyl fluoride, 0.2% NP-40, 5 ug/ml leupeptin, Sigma phosphatase inhibitor cocktail, and Sigma protease inhibitor cocktail. Cell lysates were incubated overnight with a mouse monoclonal anti-TNFR-1 cross-linked to anti-mouse IgG agarose with DMP. The IgG agarose pellet was washed and bound proteins eluted by incubation with 2×SDS-PAGE sample buffer for 5 min at 95° C. Immunoprecipitated proteins were run on a 4-12% gradient SDS-PAGE and transferred to nitrocellulose membranes. Co-immunoprecipitation of TRAF-2 and other proteins were quantitated by densitometry analysis of western blots and the values expressed in arbitrary densitometry units (ADU).

δ-PKC Activation:

The effectiveness of intra-tracheal delivery of the cell permeant dominant negative δ-PKC TAT peptide was determined by monitoring δ-PKC activity in lung tissue homogenates. δ-PKC activity was determined by phosphorylation of δ-PKC (Thr505) by western blot analysis using a phospho-specific δ-PKC (Thr505) antibody. Equal protein loading was determined by Western blot analysis for total δ-PKC.

Caspase 3 Measurements:

Caspase 3-like protease activity was measured as described previously (Kilpatrick, L. et al. (2002) Amer. J. Physiol. Cell Physiol. 283:C48-C59) by monitoring the cleavage of rhodamine 110 bis-(N-CBZ-L-aspartyl-L-gluamyl-L-valyl-L-aspartic acid amine) (Z-DEVD-R110). Human neutrophils ($1.5 \times 10^6$/150 ul) were pretreated with buffer, δ PKC–Tat peptide (1 uM), or Tat carrier peptide (1 uM) for 120 min at room temperature prior to the addition of TNF. The neutrophils were cultured for 20 hr at 37° C. in RPMI-1640+10% heat inactivated FBS. Caspase 3-like protease activity was determined in cell lysates using the EnzChek Caspase-3 Assay kit #2 (Molecular Probes, Eugene, Oreg.). Background fluorescence was determined measuring substrate cleavage in the presence of the Caspase 3 inhibitor Ac-DEVD-CHO. Results are expressed as Arbitrary Fluorescence Units (AFU).

Superoxide Anion Generation:

The generation of superoxide anion ($O_2^-$) was measured as superoxide dismutase inhibitable cytochrome c reduction (Korchak et al Biochim. Biophys. Acta 1773:440 (2007). For studies with non-adherent neutrophils, cells were activated by 1 uM fMet-Leu-Phe in the presence of 5 ug/ml cytochalasin B. For studies with adherent cells, neutrophils were incubated in FN-coated 96 well plates at a concentration of $1 \times 10^6$ cells/well at 37° C. for 30 min prior to the addition of TNF. For experiments examining the role of δ-PKC, α-PKC or β-PKC in $O_2$ generation, neutrophils were pretreated with buffer, δ PKC–Tat peptide (1 μM), α PKC–Tat peptide (1 uM), β PKC–Tat peptide (1 uM), or Tat carrier peptide (1 uM) as described previously (Kilpatrick, L. et al. J. Leuk. Biol. 80:1512 (2006), Korchak et al Biochim. Biophys. Acta 1773: 440 (2007).

Measurement of PDK1 Phosphorylation:

Neutrophils ($20 \times 10^6$ cells/well) were incubated in suspension or in FN-coated 6 well plates at 37° C. Following incubation with buffer or TNF (50 ng/ml) at 37° C. for varying time intervals, the cells were harvested and cell lysates prepared. The cells were lysed in lysis buffer containing 10 mM Hepes pH 7.4, 150 mM NaCl, 5 mM EDTA, 1 mM Na-orthovanadate, 20 uM 4-(2-aminoethyl)-benzenesulfonyl fluoride, 1% triton X-100, 5 ug/ml leupeptin, Sigma phosphatase inhibitor cocktail, and Sigma protease inhibitor cocktail. Protein concentrations of the cell lysates were determined by the BCA protein assay kit according to the manufacturer's instructions (Pierce). Cell lysates were run on 4-12% SDS-PAGE gels at a protein concentration of 30 ug/lane. PDK1 activation was determined by immunoblotting of cell lysates using a phospho-specific antibody for PDK1 (Ser241). Equal loading of PDK1 was confirmed by reprobing membranes using an antibody that recognizes both phosphorylated and non-phosphorylated forms of PDK1. For experiments examining the role of PI 3-kinase in PDK1 activation, neutrophils were incubated with the PI 3-kinase inhibitor LY 294002 (10 uM) for 20 min prior to the addition of TNF.

Immunoprecipitation of δ-PKC:

Neutrophils ($50 \times 10^6$ cells/condition) were maintained in suspension or plated onto FN-coated wells and incubated for 30 min at 37° C. Samples were then incubated with TNF (50 ng/ml) or buffer for 5 min and placed on ice. The cells were lysed in immunoprecipitation (IP) buffer and vortexed for 20 min at 4° C. to solubilize the membrane fraction. The IP buffer consisted of 10 mM Hepes, pH 7.4, 150 mM NaCl, 5 mM EDTA, 1 mM Na-orthovanadate, 20 uM 4-(2-aminoethyl)-benzenesulfonyl fluoride, 0.2% NP-40, 5 ug/ml leupeptin, Sigma phosphatase inhibitor cocktail, and Sigma protease inhibitor cocktail. For δ-PKC IP experiments, cell lysates were incubated overnight at 4° C. with a rabbit polyclonal anti-δ-PKC and then with A/G PLUS agarose for 1 hour at 4° C. The agarose pellet was washed and δ-PKC was eluted by incubation with 2×SDS-PAGE sample buffer for 5 min at 95° C. Immunoprecipitated δ-PKC was run on a 4-12% gradient SDS-PAGE and transferred to nitrocellulose membranes. Phosphorylation of δ-PKC was determined by Western blot analysis using phospho-specific antibodies (phospho-δ-PKC (Thr505) and phospho-δ-PKC (Ser643). Equal loading of δ-PKC was confirmed by reprobing membranes using antibodies that recognize both phosphorylated and non-phosphorylated forms of δ-PKC.

Statistical Analysis:

Results are expressed as means±SE. Data were analyzed by Student's t-test for two group comparisons or ANOVA for multiple comparisons. The Tukey-Kramer multiple comparisons post-test was used to evaluate the significance between experimental groups. Differences were considered significant when $P<0.05$.

It is understood that modifications which do not substantially affect the activity of the various embodiments of this invention are also provided within the definition of the invention provided herein. Accordingly, the following examples are provided to illustrate an embodiment of the invention. They are not intended to limit the scope of the invention in any way.

Example 1

As previously described, δPKC is a critical regulator of TNF anti-apoptotic signaling in neutrophils and is required for TNF-mediated activation of NFκB in neutrophils. Both p38 MAPK and ERK1/2 have important functions in the inflammatory response. These kinases, either independently or through overlapping signaling, have been implicated in the regulation of respiratory burst activity, priming, degranulation, adherence, and cytokine production. Both ERK1/2 and p38 MAPK are thought to be important in controlling neutrophil apoptosis, and ERK1/2 has been shown to be an important regulator of granulocyte macrophage-colony stimulating factor (GM-CSF), lipopolysaccharide (LPS), and interleukin-8 (IL-8) anti-apoptotic signaling.

TNF-Mediated Regulation of ERK 1/2 and JNK, But Not p38 MAPK by δPKC

Figure 3:
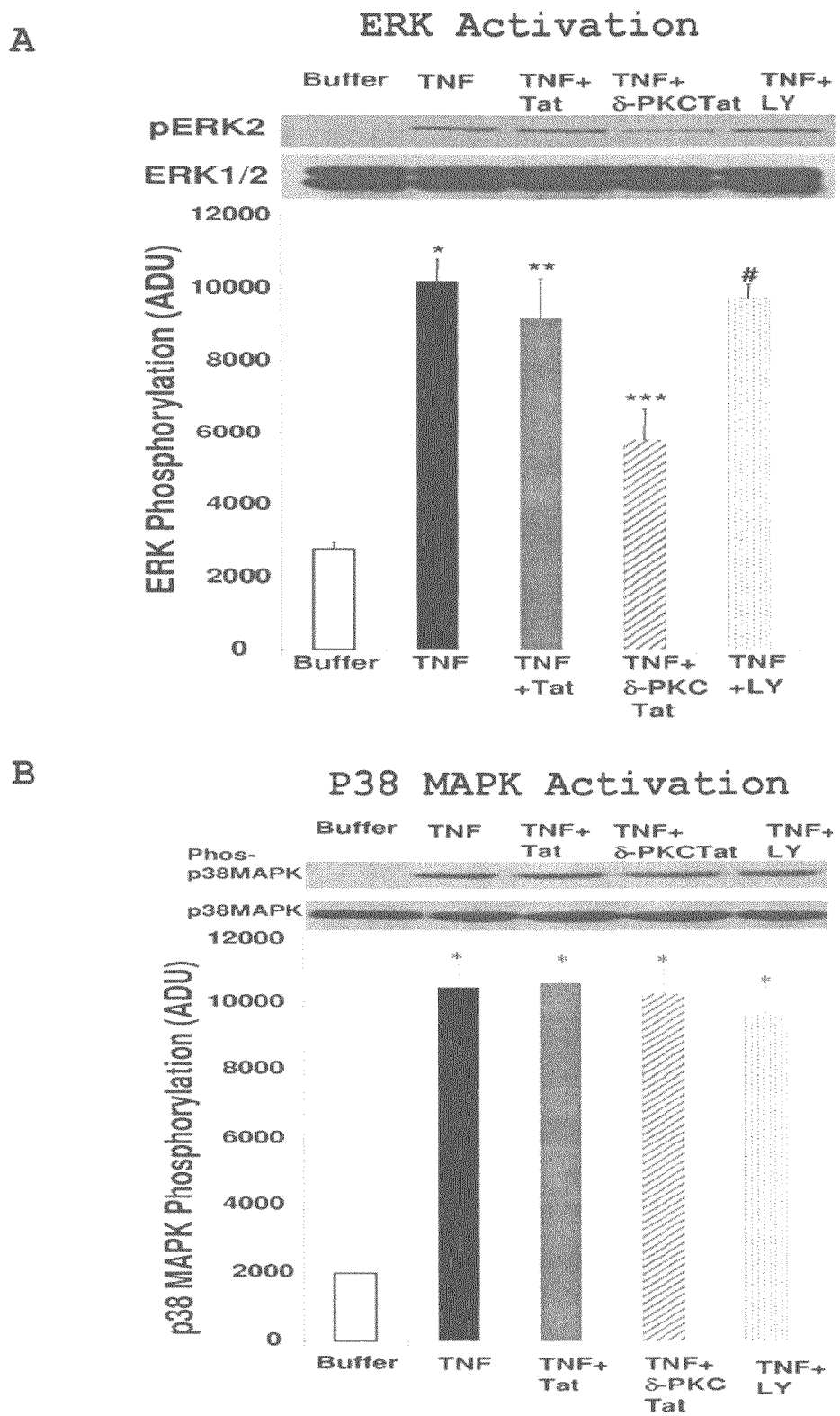
FIG. 3. TNF-mediated activation of ERK1/2 and p38 MAPK: Role of δ-PKC and PI 3-kinase TNF-mediated phosphorylation of ERK2 and p38 MAPK was determined in neutrophils incubated in the absence or presence of the specific δ-PKC inhibitor δV1.1 PKC-Tat peptide (1 μM), Tat carrier peptide (1 μM) or LY294002 (10 μM) before the addition of TNF. Neutrophils were then incubated with buffer or TNF for 5 min. ERK2 and p38 MAPK activation was determined by Western blot analysis using phosphospecific ERK1/2 and p38 MAPK antibodies. (A) ERK2 activation: *, P<0.01 buffer vs. TNF; , P<0.01 buffer vs. TNF+Tat; *, buffer vs. TNF+δPKC–Tat, TNF+Tat vs. TNF+δPKC–Tat, TNF vs. TNF+δPKC–Tat; and #, P<0.01 buffer vs. TNF+LY (n=4). (B) p38 MAPK Activation: *, P<0.01, vs. buffer (n=4).

Two different approaches were used to determine whether δPKC was also a positive regulator of MAP kinase activation. Human neutrophils were pre-treated with the δV1-1 PKC–Tat peptide. TNF triggered phosphorylation of ERK2 was significantly depressed when neutrophils were pretreated with the δV1.1 PKC–Tat peptide as compared with neutrophils treated with TNF alone or TNF+Tat carrier (FIG. 3A). Conversely, δV1.1 PKC–Tat pretreatment had no significant effect on TNF-mediated activation of p38 MAPK (FIG. 3B). PI-3-kinase is also involved in TNF-mediated suppression of caspase 3 activity. To ascertain whether PI 3-kinase had a role in TNF-mediated MAPK signaling, the effect of the PI-3-kinase inhibitor on ERK2 and p38 MAPK phosphorylation was examined. TNF-mediated activation of either ERK2 or p38 MAPK is PI 3-kinase independent. Thus, TNF activation of ERK and p38 MAP kinase does not require cooperative signaling between β-integrins and TNF signaling. δPKC is a positive regulator of ERK1/2 activation but has no regulatory role in p38 MAPK activation indicating differential regulation of these MAP Kinases by TNF.

Figure 4:
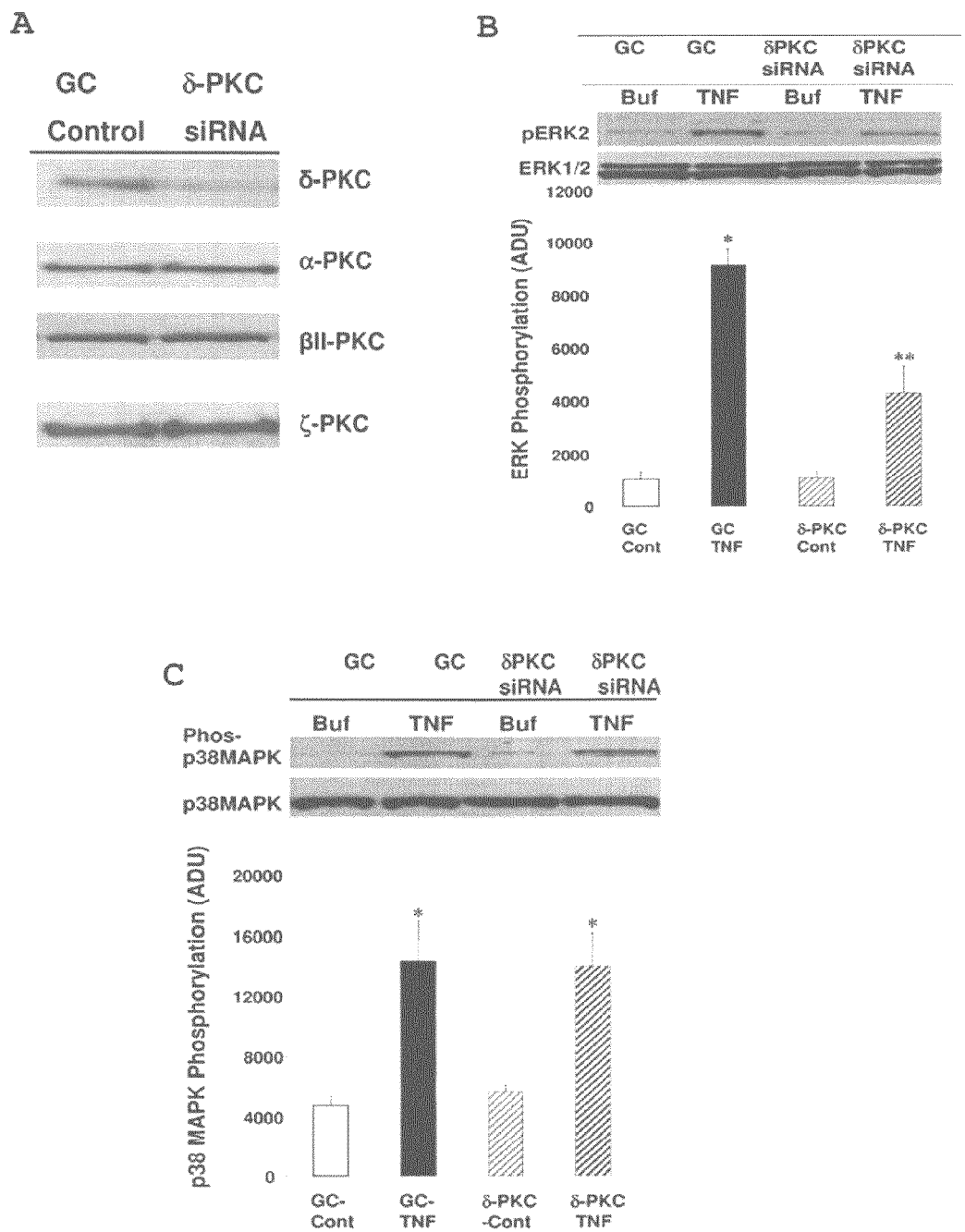
FIG. 4. Effect of δ-PKC depletion by siRNA on ERK1/2 and p38 MAPK activation in differentiated HL-60 cells. (A) Selective depletion of δ-PKC by stealth δ-PKC siRNA in differentiated HL60 (dHL60) cells. (Representative Western blots from 4 separate experiments). Levels of specific PKC isotypes were determined in cell lysates by immunoblotting with isotype-specific antibodies to α-PKC, β-PKC, δ-PKC and ι-PKC. (B) Effect of δ-PKC depletion on ERK2 activation. dHL-60 cells were incubated in the presence or absence of TNF (50 ng/ml) after transfection with δ-PKC stealth siRNA (δ-PKC siRNA) or with siRNA containing equivalent % GC nucleotide content (GC-control). Representative Western blots from 4 separate experiments. Densitometry analysis of TNF mediated ERK2 activation in dHL60 cells transfected with GC control siRNA or δ-PKC siRNA. Values are expressed as means±SE (n=4 separate neutrophil preparations) and are expressed in arbitrary densitometry units. *Statistical significance P<0.01, GC Cont vs. GC+TNF; **P<0.01, δ-PKC Cont vs. δ-PKC+TNF and GC+TNF vs. δ-PKC+TNF. (C) Densitometry analysis of TNF-mediated p38 MAPK activation in dHL60 cells transfected with GC control siRNA or δ-PKC siRNA. *, P<0.01, GC Cont vs. GC+TNF and δ-PKC Cont vs. δ-PKC+TNF.

Depletion of δPKC by siRNA in dHL-60 Cells: Effect on TNF-Mediated Activation of MAPK To further confirm the role of δPKC in TNF-mediated activation of ERK1/2, HL60 cells differentiated to a neutrophilic phenotype were depleted of δPKC. dHL-60 cells also contain the PKC isotypes α, βII and ζ. Pretreatment with Stealth δPKC siRNA selectively depleted δPKC, but not α, βII or ζ-PKC (FIG. 4A). Similar to neutrophils, TNF activates both ERK1/2 and p38 MAPK in dHL60 cells (FIGS. 4B and 4C, lanes 1-2). As shown in FIG. 4B, lanes 3-4, TNF-mediated ERK2 phosphorylation in dHL60 cells depleted of δPKC was significantly decreased as compared with GC controls (47% of GC control, $P<0.01$). The level of p38 MAPK phosphorylation in response to TNF was comparable in dHL60 cells transfected with either GC control siRNA or δPKC siRNA (P=NS, FIG. 4C). These results provide further evidence of the regulatory role of δPKC in TNF-mediated ERK1/2 activation but not in p38 MAPK activation regarding anti-apoptotic TNF signaling.

Figure 5:
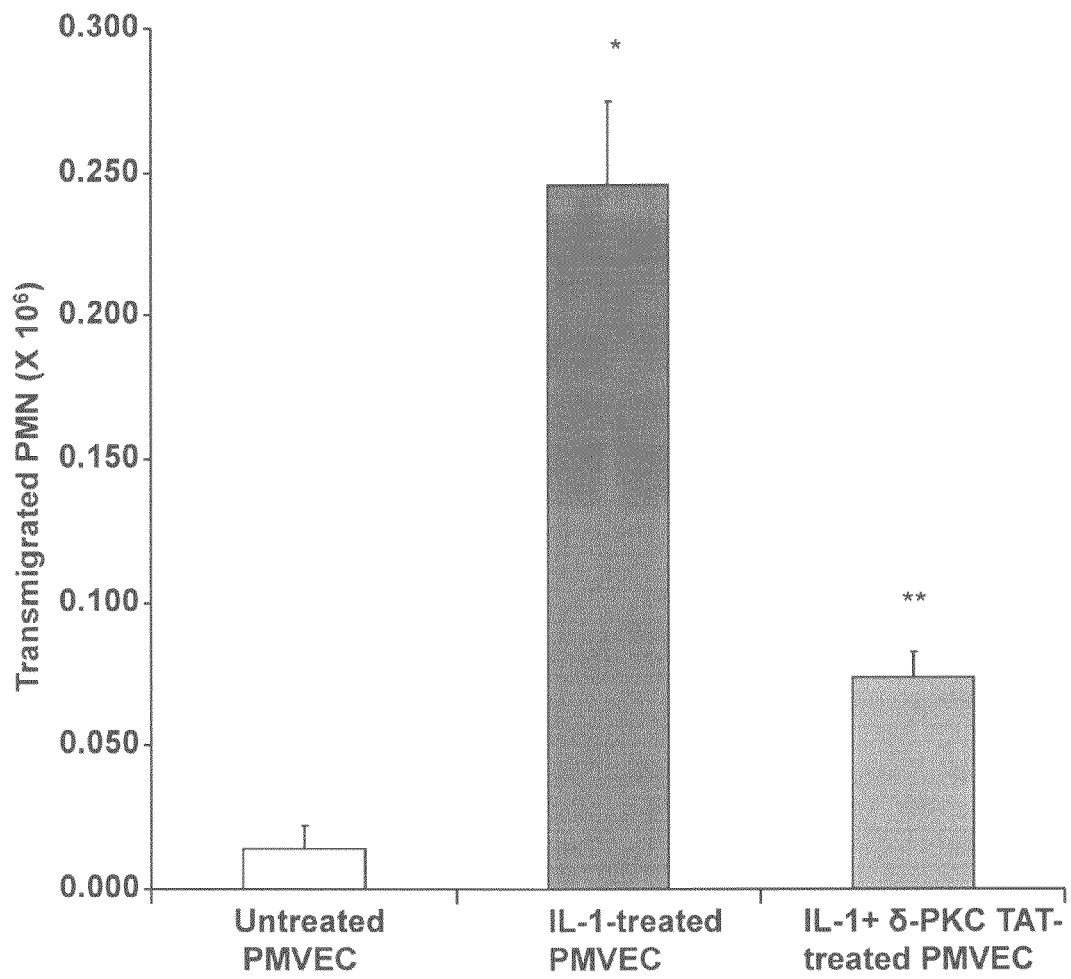
FIG. 5. Neutrophil transmigration is significantly enhanced through cytokine-activated human pulmonary microvascular cells (PMVEC) and is δ-PKC dependent. Neutrophils ($2 \times 10^6$ cells/well) were allowed to transmigrate through buffer-treated, IL-1-treated, or IL-1+δ-PKC TAT-treated PMVEC for 3 hrs. (Mean±SEM, n=12–16) *P<0.001 transmigration through untreated PMVEC vs. IL-1 treated PMVEC, **P<0.01 IL-1-treated PMVEC vs. IL-1+δ-PKC TAT-treated PMVEC.

Neutrophil Transmigration is Significantly Enhanced Through Cytokine-Activated Human Pulmonary Microvascular (PMVEC) and is δ-PKC Dependent As shown in FIG. 5, IL-1 pretreatment of PMVEC monolayers significantly enhanced neutrophil transmigration as compared to migration through untreated PMVEC. Inhibition of δ-PKC activity with the dominant negative δ-PKC TAT peptide significantly inhibited transmigration of neutrophils through cytokine-activated PMVEC. Thus, neutrophil transmigration through cytokine-activated PMVEC, a β2-integrin dependent process, requires δ-PKC.

Example 2

Preclinical Model of ARDS

Figure 6:
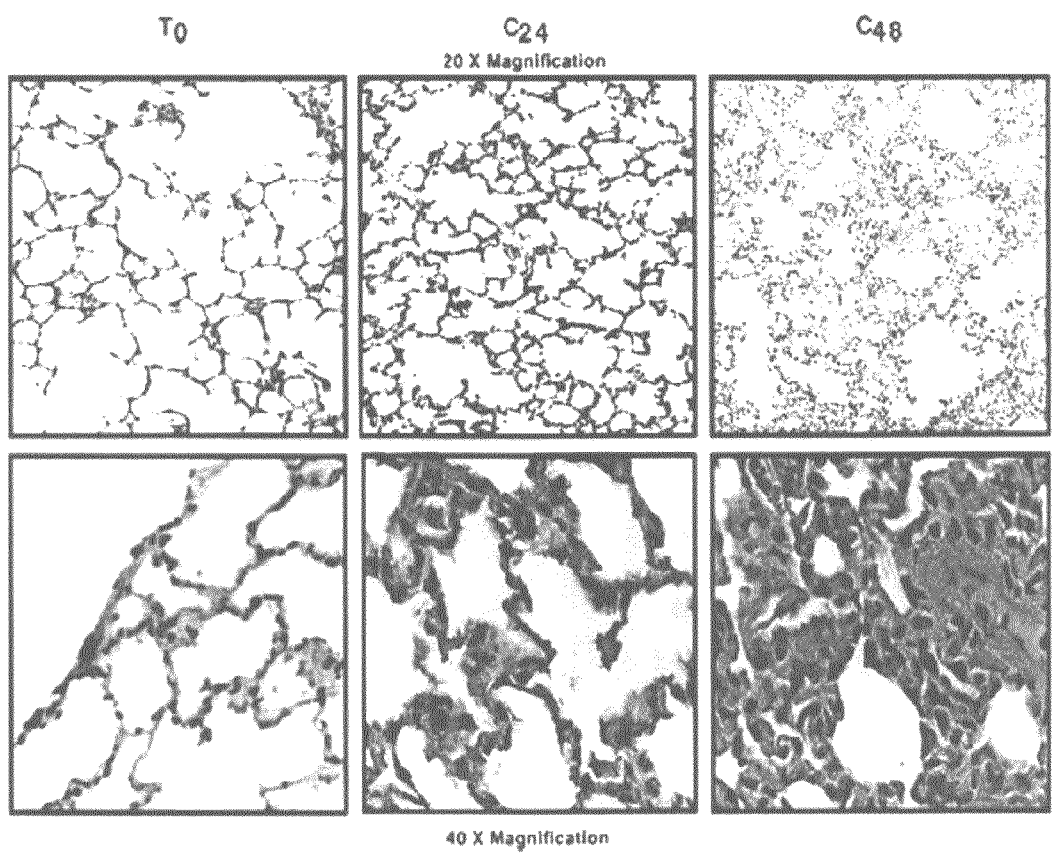
FIG. 6. Effect of 2CLP on Lung Pathology. Lung sections were obtained after cecal ligation and double puncture (2CLP) and stained with hematoxylin and eosin. (Top) Magnification (20×) of sections obtained at 0 time (T0), 24 hrs (C24), and 48 hr (C48) after 2CLP. (Bottom) Magnification (40×) of section obtained 24 hrs following 2CLP. Arrows indicate neutrophils.

The preclinical animal studies use a well-characterized rat model of ARDS that has been used extensively in laboratories (Weiss, Y. G., et al. (2001) Anesthesiology 95, 974-82; Weiss, Y. G., et al. (2002) J Clin Invest 110, 801-6; Weiss, Y. G., et al. (2007) Crit Care Med.). This clinically relevant animal model produces lung injury by an indirect insult, intra-abdominal sepsis, a type of injury that occurs in most surgical patients who develop ARDS. Cecal ligation and double puncture (2CLP) induces severe sepsis accompanied by the lung pathology typical of ALI/ARDS. This model is characterized by hypoxemia, tachypnea, neutrophil infiltration, and capillary leak into the lung (Weiss, Y. G., et al. (2001) Anesthesiology 95, 974-82; Weiss, Y. G., et al. (2002) J Clin Invest 110, 801-6; Weiss, Y. G., et al. (2007) Crit Care Med.). As shown in FIG. 6, hematoxylin and eosin (H+E)-stained sections confirmed the presence of significant numbers of neutrophils in the lung. 2CLP also produced septal thickening, increased cellularity, and proteinacious exudates, typical features of the lung pathology observed during clinical ARDS (Weiss, Y. G., et al. (2001) Anesthesiology 95, 974-82; Weiss, Y. G., et al. (2002) J Clin Invest 110, 801-6; Weiss, Y. G., et al. (2007) Crit Care Med.). Quantitation of neutrophils in H+E-stained sections indicated that there were very few neutrophils present in the lungs of animals that had either no surgery or sham surgery (12±4 and 17±6 neutrophils/field in fixed lung parenchyma, respectively). However, 48 hr after 2CLP there was a dramatic increase in neutrophil accumulation to 914±156 neutrophils/field in fixed lung parenchyma (Weiss, Y. G., et al. (2002) J Clin Invest 110, 801-6).

Activation of NFκB in Rat Lungs Following 2CLP

Activation of the nuclear transcription factor NFκB is an important regulator of pro-inflammatory signaling. The role of NFκB in inflammatory lung injury and ARDS is well established (Christman, J. W., et al. (2000) Chest 117, 1482-7). 2CLP activates NFκB in the rat lung. As shown in FIG. 7, 48 hrs following 2CLP surgery, there was a significant increase in DNA binding of the p50/p65 NFκB heterodimer as determined by EMSA and increased translocation of the p65 NFκB subunit to the nuclear fractions.

2CLP Increases Cytokine-Chemokine Expression

Figure 8:
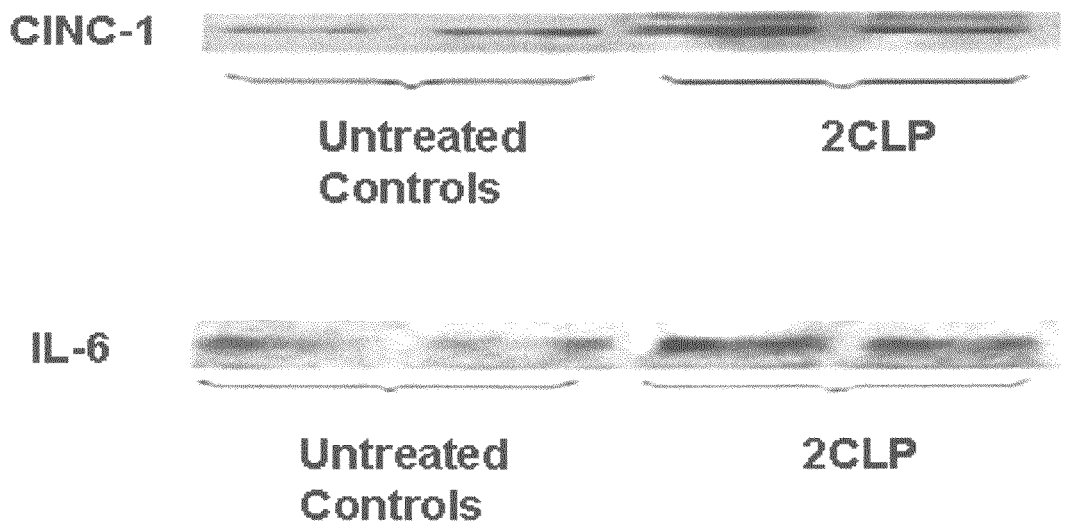
FIG. 8. 2CLP increases NFκB-dependent CINC-1 and IL-6 expression in whole lung homogenates. Representative western blot for CINC-1 and IL-6 from 3 separate experiments.

Migration of neutrophils into the lung and subsequent activation is dependent on pro-inflammatory cytokines-chemokines such as the rat chemokine CINC-1 (Cytokine Induced Neutrophil Chemoattractant) and IL-6 (interleukin-6). Expression of both CINC-1 and IL-6 in lung tissue was significantly increased 48 hrs following 2CLP as compared to untreated controls (FIG. 8). The effect of 2CLP on lung function after 24 hrs was examined, and 2CLP produces significant increases in myeloperoxidase activity in lung tissue homogenates as compared to control rats indicative of significant neutrophil infiltration of the lung within 24 hrs (Table I). Bronchoalveolar lavage (BAL) protein content was also significantly increased by 24 hrs post 2CLP surgery indicating capillary leak (Table I).

TABLE I

Effect of 2CLP on Lung Parameters 24 hours post surgery

|  | MPO (U/ml) | BAL Protein (ug/ml) |
|---|---|---|
| No Operation | 1.0 ± 0.2 | 186 ± 20 |
| 2CLP | 2.5 ± 0.3* | 612 ± 135* |

Data are expressed as mean ± SD, n = 4,
*P < 0.01 2CLP vs. no operation.

Example 3

In Vitro Studies with the Dominant Negative δ-PKC TAT Peptide

δ-PKC Regulates Cytokine-Mediated Suppression of Neutrophil Spontaneous Apoptosis δ-PKC has been identified as an important regulator of cytokine mediated anti-apoptotic and pro-inflammatory signaling in adherent neutrophils (Kilpatrick, L. E., et al. (2002) Am J Physiol Cell Physiol 283, C48-57; Kilpatrick, L. E., et al. (2004) Am J Physiol Cell Physiol 287, C633-42; Kilpatrick, L. E., et al. (2006) J Leukoc Biol. 80:1512-1521; Kilpatrick, L. E., et al. (2000) Am J Physiol Cell Physiol 279, C2011-8). Neutrophils undergo spontaneous apoptosis which can be suppressed in vitro by culturing cells in the presence of cytokines such as TNF (Kilpatrick, L. E., et al. (2002) Am J Physiol Cell Physiol 283, C48-57; Kilpatrick, L. E., et al. (2006) J Leukoc Biol. 80:1512-1521). When human neutrophils were cultured for 20 hrs in the presence of TNF (25 ng/ml), neutrophil apoptosis was significantly suppressed as compared to neutrophils cultured in buffer alone (controls) as determined by DNA fragmentation (TUNEL assay, 39.5±5% of controls, $p<0.01$, $n=4$) or by PS (phosphatidylserine) externalization (annexin V, 37±4.1% of controls, $p<0.01$, $n=3$). Activation of caspases is one of the earliest markers of apoptosis occurring upstream of DNA fragmentation and PS externalization. Caspase 3 plays a critical role in spontaneous neutrophil apoptosis (Kilpatrick, L. E., et al. (2002) Am J Physiol Cell Physiol 283, C48-57; Daigle, I., Simon, H. U. (2001) Int Arch Allergy Immunol 126, 147-56; Scheel-Toellner, D., et al. (2004) Blood 104, 2557-64). Caspase 3 activity is also suppressed by pretreatment with TNF (45±4% of controls, $p<0.01$, $n=5$, FIG. 9)(Kilpatrick, L. E., et al. (2002) Am J Physiol Cell Physiol 283, C48-57; Kilpatrick, L. E., et al. (2006) J Leukoc Biol. 80:1512-1521). Initial studies demonstrated this suppression of neutrophil apoptosis by TNF was inhibited by pretreatment with the kinase inhibitor rottlerin suggesting a regulatory role for δ-PKC in anti-apoptotic signaling. However, recent reports have raised issues about the specificity of rottlerin as a δ-PKC inhibitor (Davies, S. P., et al. (2000) Biochem J 351, 95-105). To establish a role specifically for δ-PKC in the TNF-mediated anti-apoptotic signaling, a more specific inhibitor is required. A highly specific δ-PKC antagonist has recently been reported (Chen, C., Mochly-Rosen, D. (2001) J Mol Cell Cardiol 33, 581-5). This δ-PKC peptide antagonist is derived from the first unique variable region of δ-PKC and coupled to a membrane permeant peptide sequence in the HIV tat gene product. The δ-PKC TAT peptide through inhibition of the activation of δ-PKC in essence produces a dominant negative kinase that is unique to δ-PKC and does not affect other PKC isotypes such as α-PKC, β-PKC or ζ-PKC (Kilpatrick, L. E., et al. (2004) Am J Physiol Cell Physiol 287, C633-42; Kilpatrick, L. E., et al. (2006) J Leukoc Biol. 80:1512-1521; Chen, L., et al. (2001) Proc Natl Acad Sci U S A 98, 11114-9; Souroujon, M. C., Mochly-Rosen, D. (1998) Nat Biotechnol 16, 919-24).

Figure 9:
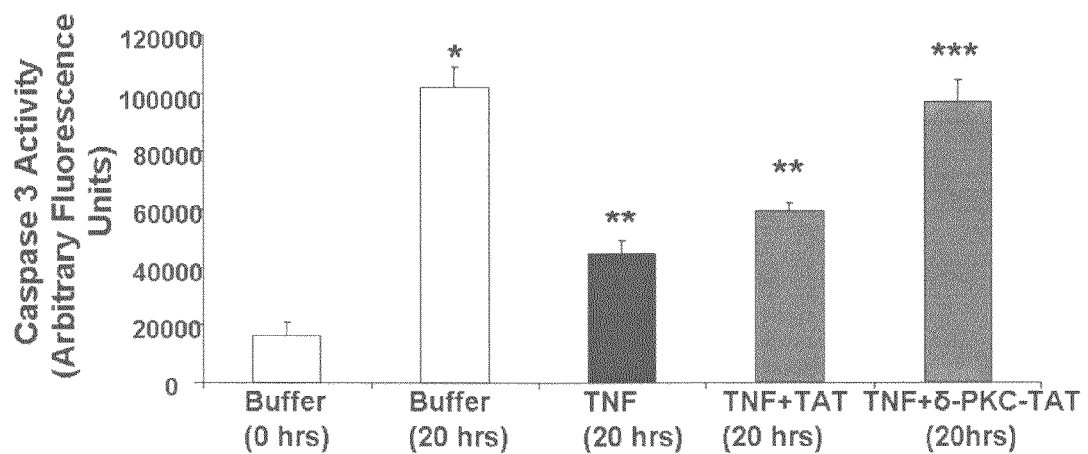
FIG. 9. TNF Mediated Suppression of Caspase 3 Activity: Role for δ-PKC. Caspase 3 activity was determined in cell lysates prepared from neutrophils cultured for 0 and 20 hrs. Neutrophils were cultured+/−TNF (25 ng/ml). δ-PKC TAT peptide inhibitor (luM) or the TAT carrier dimer (luM) were added 1 hr prior to the addition of TNF. Results are mean±SEM, n=5. *p<0.01 Buffer (0 hr) vs. Buffer (20 hrs), p<0.01 Buffer (20 hrs) vs. TNF, Buffer (20 hrs) vs TNF+TAT (20 hrs), *p<0.01 TNF+δ-PKC–TAT vs. TNF and vs. TNF+TAT.

Pretreatment of neutrophils with this dominant negative cell permeant δ-PKC TAT peptide significantly attenuated the inhibitory effect of TNF on caspase 3 activity indicating that TNF-mediated anti-apoptotic signaling is δ-PKC dependent (FIG. 9).

Neutrophil migration from the peripheral circulation into the lungs is a critical early event in the development of ARDS and requires neutrophil migration through the endothelium. Transmigration of neutrophils through cytokine-activated endothelium suppresses neutrophil spontaneous apoptosis, a process that requires β2-integrins and is critical for development of ARDS (Coxon, A., et al. (1999) Journal of Experimental Medicine 190, 923-34; McGettrick, H. M., et al. (2006) J Leukoc Biol 79, 779-88). To determine whether the regulatory role of δ-PKC is unique to TNF signaling or a common mechanistic pathway utilized by other proinflammatory mediators, a physiologically relevant in vitro model of neutrophil transmigration across human pulmonary artery endothelial (HPAE) cell monolayers was used. As shown in Table II, migration through IL-1-activated endothelial monolayers inhibited caspase 3 activity as compared to neutrophils which had migrated through untreated HPAE cell monolayers. Migration-dependent suppression of caspase 3 activity was inhibited by incubation with the dominant negative cell permeant δ-PKC TAT peptide indicating that transmigration-dependent suppression of neutrophil apoptosis is also δ-PKC dependent. Thus, δ-PKC is an important signal transducer of anti-apoptotic signaling for multiple pro-inflammatory mediators.

TABLE II

Suppression of Neutrophil Caspase 3 Activity by Transendothelial Migration: Role for δ-PKC

| Conditions | Caspase 3 Activity (AFU) |
|---|---|
| Untreated HPAE monolayers | 100,165 ± 6,989 |
| IL-1 treated HPAE monolayers | 55,027 ± 10,332* |
| IL-1 treated HPAE monolayers + δ-PKC TAT Peptide (1 uM) | 85,742 ± 8,302** |

Figure 10:
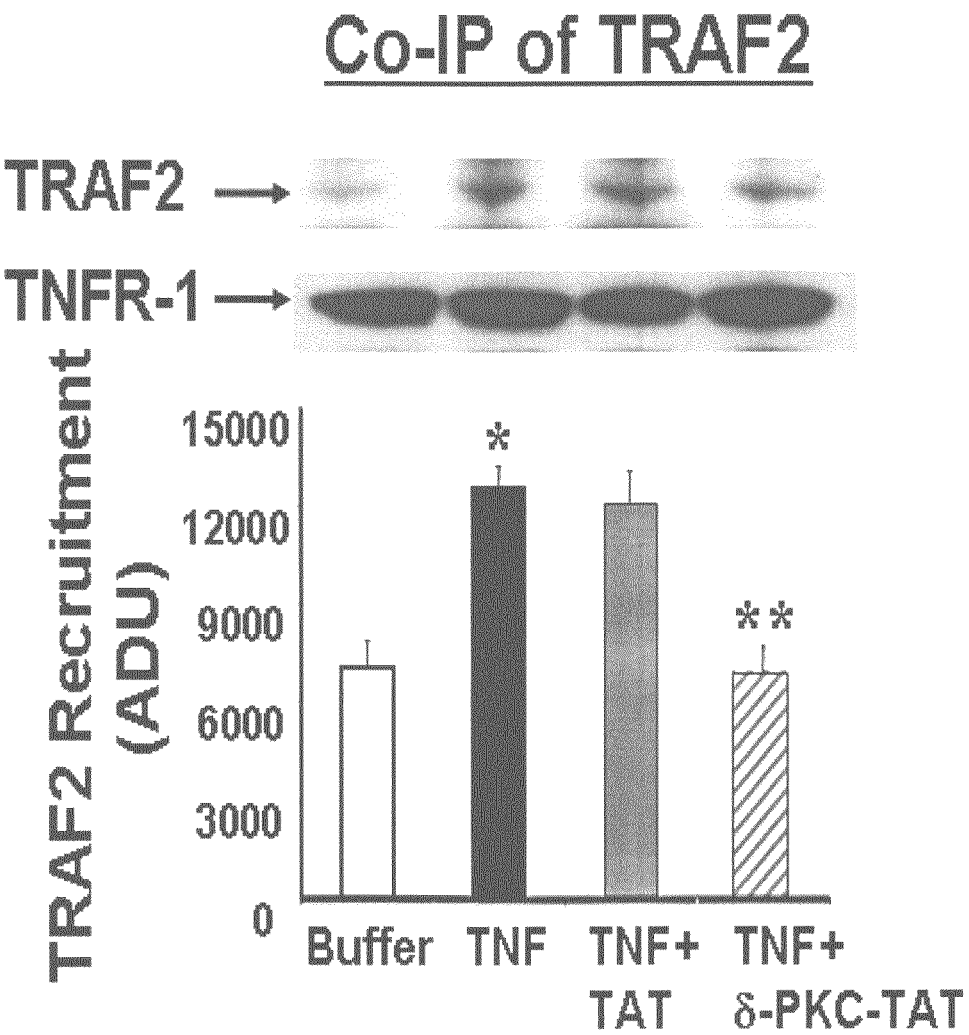
FIG. 10. Role of δ-PKC in TNF Mediated Assembly of TNFR-1 Signaling Complex. TNFR-1 was immunoprecipitated (IP) from adherent neutrophils and Co-IP of TRAF2 determined by Western Blotting. Neutrophils were pretreated with δ-PKC–TAT (luM), TAT carrier (luM) or buffer prior to addition of buffer or TNF. Values are Mean±SEM (n=5) *P<0.001 Buffer vs. TNF, **P<0.01 TNF+δ-PKC–Tat vs. TNF+Tat and TNF+δ-PKC–Tat vs. TNF.

Human pulmonary artery endothelial (HPAE) monolayers were cultured ± IL-1 (10 U/ml) overnight, washed, and $2 \times 10^6$ neutrophils added. After 3 hr incubation, migrated cells were collected and caspase 3 activity measured following 20 hr incubation. Mean ± SEM, n = 5,
*$p < 0.01$ caspase 3 activity after migration through IL-1 treated monolayer,
**$p < 0.01$ caspase 3 activity following migration through IL-treated monolayer vs. IL-1-treated monolayer + δ-PKC TAT peptide δ-PKC Regulates TNF-Mediated Activation of NFκB Cytokines activate multiple signaling pathways in the neutrophil involved in anti-apoptotic signaling. Experimental studies have identified the transcription factor NFκB as a required element in TNF anti-apoptotic signaling (Kilpatrick, L. E., et al. (2002) Am J Physiol Cell Physiol 283, C48-57; Kilpatrick, L. E., et al. (2004) Am J Physiol Cell Physiol 287, C633-42; Kilpatrick, L. E., et al. (2006) J Leukoc Biol. 80:1512-1521). Furthermore, using the dominant negative cell permeant δ-PKC TAT peptide, an important role for δ-PKC in the activation of NFκB by TNF was established. The assembly of a multi-component signaling complex that includes TNFR-1 and the effector proteins TRADD, RIP and TRAF2 controls activation of NFκB. Co-IP studies demonstrated that δ-PKC was required for the recruitment of TRAF2 to the TNFR-1 signaling complex (FIG. 10). Pretreatment with the TAT carrier peptide alone did not alter TNF-mediated recruitment of TRAF2 to the TNFR-1 signaling complex. Thus, δ-PKC regulates the assembly of the TNFR-1:TRADD:TRAF2:RIP signaling complex and TNF mediated anti-apoptotic signaling.

Example 4

Role of δ-PKC in Pro-Inflammatory Signaling

δ-PKC Regulates TNF Triggered $O_2^-$ Generation

Figure 11:
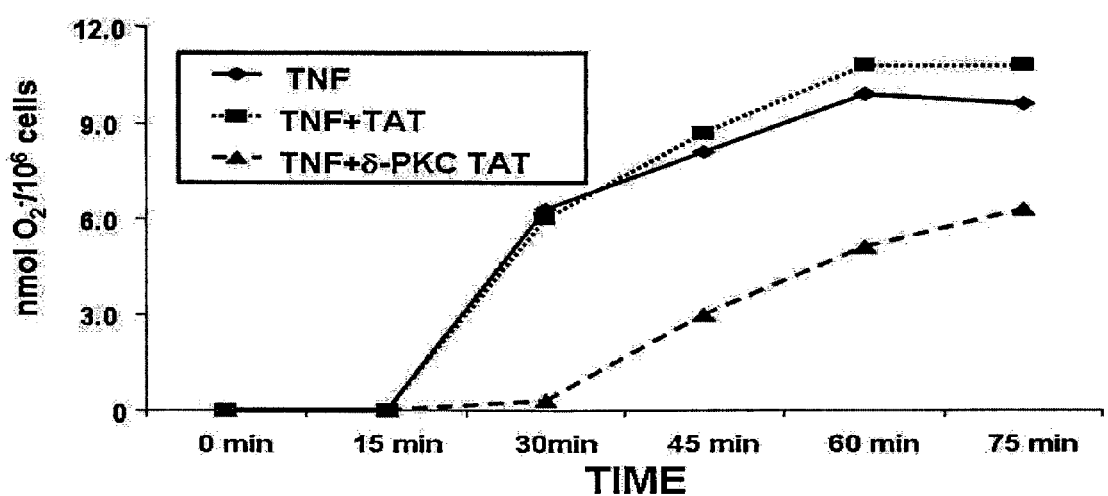
FIG. 11. TNF Mediated $O_2-$ Generation in Adherent Neutrophils: Role of δ-PKC. FN-adherent neutrophils were pretreated with δ-PKC TAT peptide inhibitor (1 uM), TAT carrier peptide (1 uM), or buffer alone prior to the addition of TNF (25 ng/ml). $O_2-$ generation was measured as superoxide anion dismutase (SOD)-inhibitable reduction of cytochrome c. Results are expressed as nmol $O_2-/10^6$ cells (n=4 separate neutrophil preparations).
Figure 12:
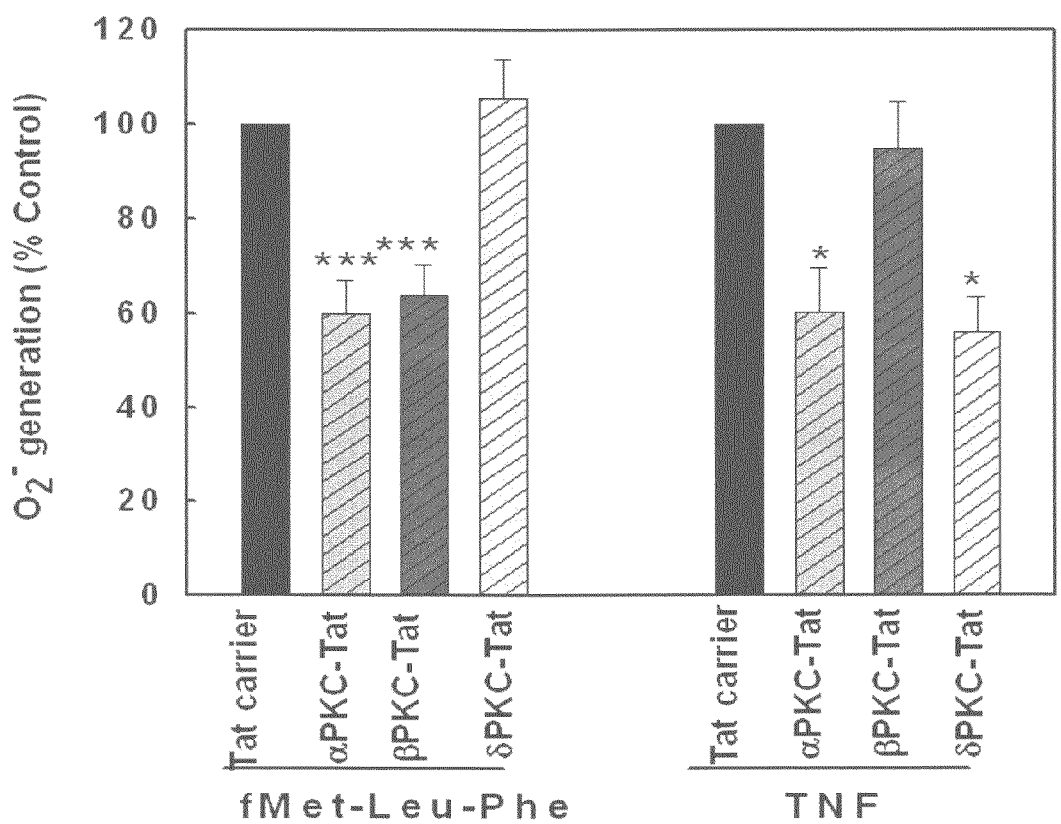
FIG. 12. PKC isotype selectivity in signaling for $O_2-$ generation. δ-PKC selectively regulates adherence dependent $O_2-$ generation but not adherence independent $O_2-$ generation. $O_2-$ generation was measured in neutrophils pretreated with 1 uM TAT-peptide, α-PKC–TAT, β-PKC–TAT or δ-PKC–TAT prior to addition of 1 μM fMet-Leu-Phe in suspended cells, or 25 ng/ml TNF in adherent neutrophils. ***P<0.001 or *p<0.04 TAT-carrier vs TAT–PKC inhibitor (n=5).

Oxygen radicals such as superoxide anion ($O_2^-$) are key components of host defense but, if not appropriately regulated, can also damage host tissue. In neutrophils, TNF only triggers $O_2^-$ generation in adherent neutrophils when β2-integrins are engaged (Nathan, C. F. (1987) J Clin Invest 80, 1550-60). TNF triggered $O_2^-$ generation was significantly decreased by pretreatment with the dominant negative δ-PKC–TAT peptide indicating δ-PKC is a positive regulator of $O_2^-$ generation (FIG. 11). Pretreatment with the TAT carrier alone had no significant effects on $O_2^-$ production. Thus, δ-PKC is required for both TNF anti-apoptotic and pro-inflammatory signaling. To ascertain whether the regulatory role of δ-PKC in $O_2^-$ generation was adherence dependent, the role of different PKC isotypes in adherent dependent and adherent independent $O_2^-$ generation was determined. Using cell-permeant TAT-linked antagonist peptides from the V5 region of α-PKC and βII-PKC, the V1 region of δ-PKC, and a control TAT carrier (Begley, R., et al. (2004) Biochem Biophys Res Commun 318, 949-54; Souroujon, M. C., Mochly-Rosen, D. (1998) Nat Biotechnol 16, 919-24), it was shown that $O_2^-$ generation triggered by the bacterial peptide fMet-Leu-Phe was α-PKC and β-PKC-dependent but δ-PKC independent (FIG. 12). Thus, δ-PKC is not essential for activation of $O_2^-$ generation by fMet-Leu-Phe in neutrophils in suspension. These findings are consistent with previous studies in HL-60 cells differentiated to a neutrophillic phenotype (dHL-60) (Korchak, H. M., et al. (2007) Biochim Biophys Acta 1773, 440-449). Depletion of δ-PKC in dHL60 cells by stealth siRNA treatment had no significant effect on $O_2^-$ generation elicited by either fMet-Leu-Phe or PMA. In contrast to fMet-Leu-Phe triggered $O_2^-$ generation, TNF elicited $O_2^-$ generation in FN-adherent neutrophils was α-PKC and δ-PKC dependent, but β-PKC independent (FIG. 12). Thus, δ-PKC is not an essential component of all signaling pathways leading to $O_2^-$ generation and suggests a different regulatory role for δ-PKC in adherent cells.

Cooperative Signaling Between TNF and β2-Integrins Regulates δ-PKC Activity

Figure 13:
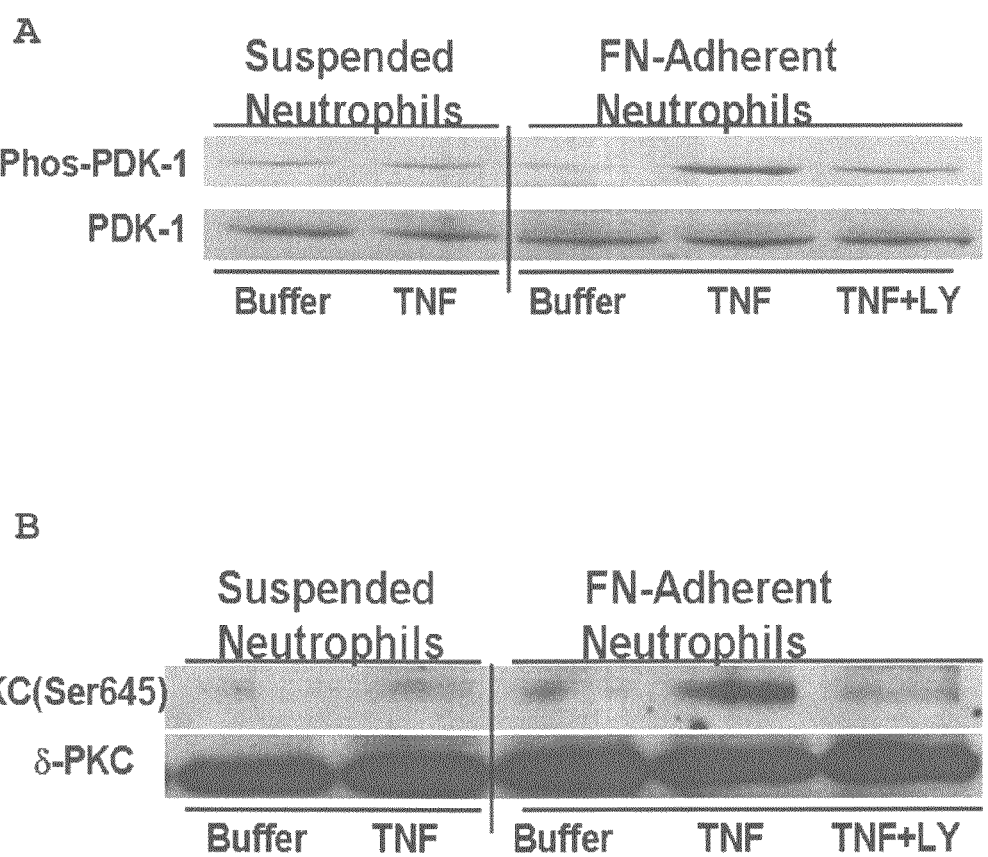
FIG. 13. (A) TNF Phosphorylates PDK-1 in Adherent Neutrophils but not in Suspended Neutrophils: Role of PI-3-Kinase. (B) TNF Only Phosphorylates δ-PKC-Ser645 in Adherent Neutrophils: Role of PI-3-Kinase.

Adherence and thus cooperative signaling between β2-integrins and cytokines could regulate δ-PKC activity through alterations in phosphorylation. PDK-1, a member of the PI-3-kinase-PDK1-Akt pathway, can phosphorylate δ-PKC in the activation loop (Thr505) which in turn leads to auto-phosphorylation of δ-PKC(Ser643) a critical site for enzyme activity (Parker, P.J., Murray-Rust, J. (2004) J Cell Sci 117, 131-2). TNF triggers activation and phosphorylation of PDK1 in adherent neutrophils but not in suspended cells (FIG. 13). Furthermore, TNF mediated activation of PDK1 was inhibited by LY294002 indicating PDK1 activation was PI 3-kinase dependent. There is little phosphorylation of δ-PKC on Ser643 in response to TNF in suspended cells (FIG. 13). Conversely, in adherent neutrophils, TNF triggered a significant increase in Ser643 phosphorylation, that was PI 3-kinase dependent. Thus, δ-PKC Ser643 phosphorylation requires integration of signals from TNF and β2-integrin activation.

Example 5

In Vivo Animal Model Studies with the δ-PKC TAT Inhibitory Peptide

Figure 14:
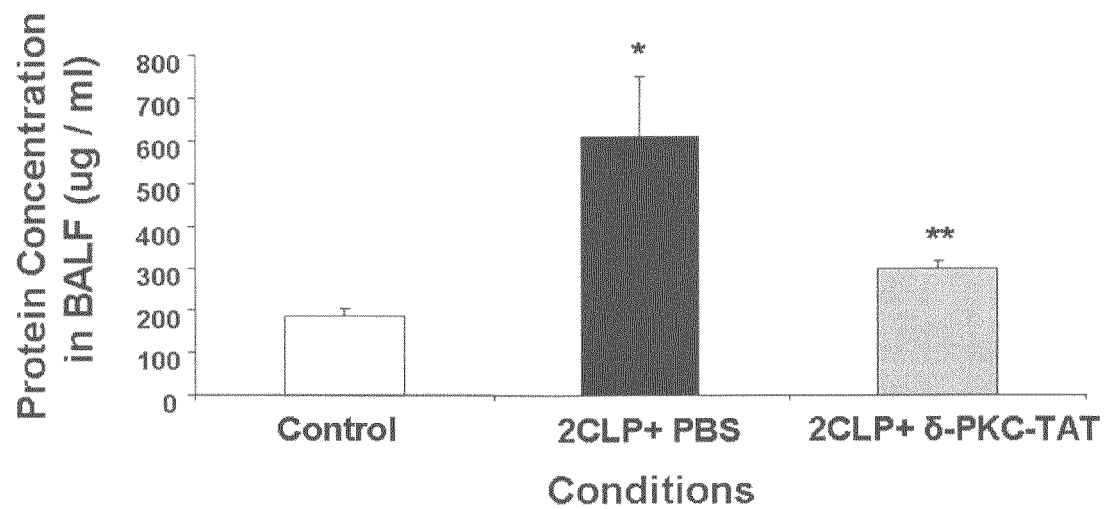
FIG. 14. Effect of Intra-tracheal Administration of δ-PKC–TAT Peptide Inhibitor on Total Protein Concentrations in BALF Following Cecal Ligation and Double Puncture. BALF was collected by instilling and withdrawing 1.5 ml of sterile PBS three times from the lungs via an intratracheal cannula (24 hrs post 2CLP). Values are mean±SEM (ug/ml) *p<0.02 Control vs. 2CLP+PBS, **p<0.05 2CLP+PBS vs. 2CLP+δ-PKC–TAT.

During in vitro experiments, one group of rats received an intra-tracheal injection of PBS following 2CLP surgery (2CLP+PBS, n=3), while a second group of rats received 200 ug/kg of the δ-PKC TAT peptide inhibitor intra-tracheally following 2CLP surgery (2CLP+δ-PKC–TAT, n=4). A third experimental animal group did not undergo surgery or intra-tracheal fluid administration (Controls, n=4). Twenty-four hours following 2CLP surgery, rats were sacrificed and BAL fluid (BALF) collected. BALF protein levels were determined as a marker for severity of lung injury. BALF protein content after 2CLP increased 3 fold as compared to controls (FIG. 14) indicating increased pulmonary endothelial permeability and capillary leak. Intra-tracheal administration of the δ-PKC TAT peptide inhibitor following 2CLP surgery significantly decreased BALF protein levels. These studies also demonstrate that the δ-PKC TAT inhibitory peptide at a dose of 200 ug/kg is well tolerated by the animals and is non-toxic. These findings indicate that the isotype selective δ-PKC TAT Peptide inhibitor exerts a lung-protective effect at 24 hrs post 2CLP.

Figure 15:
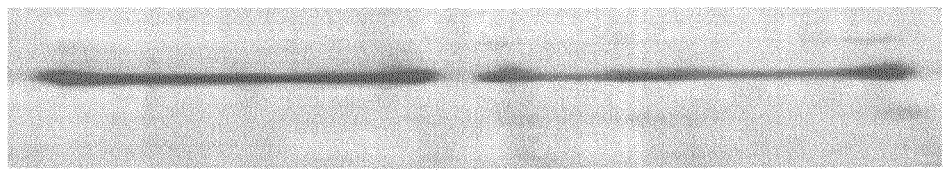
FIG. 15. Measurement of δ-PKC levels in leukocytes from BALF samples in a rat model of ARDS. BAL fluid was collected 24 hrs following 2CLP. BAL fluid was centrifuged, cell pellets collected, and lysates prepared ($3 \times 10^6$ cells/ml) Each lane contains cell lysates harvested from a single rat's BAL. Representative western of 2 independent experiments.
Figure 16:
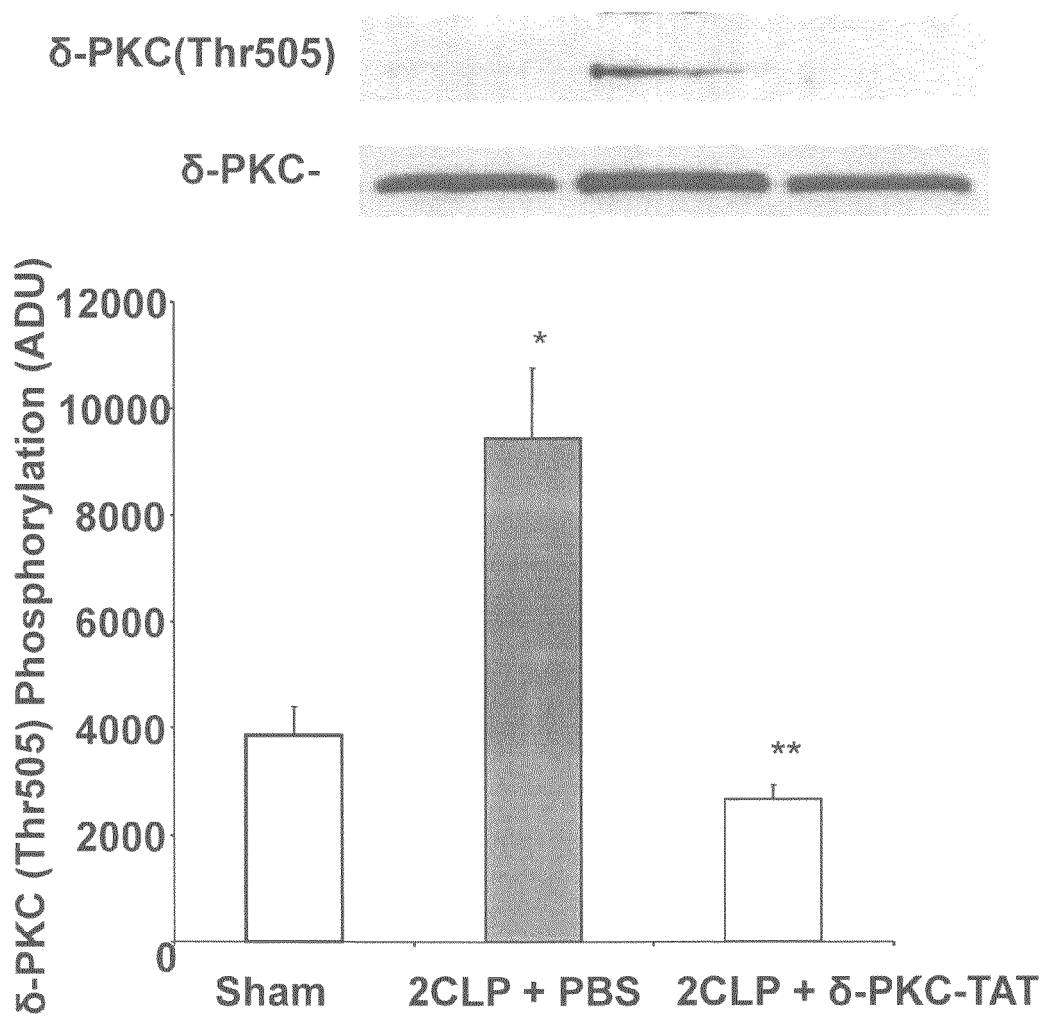
FIG. 16. Intra-tracheal administration of the δ-PKC TAT peptide inhibitor blocks 2CLP-mediated phosphorylation of δ-PKC (Thr505) in the lung. Lung tissue was harvested 24 hr post 2CLP. δ-PKC (Thr505) phosphorylation was expressed in arbitrary densitometry units (ADU), n=7–9 (Mean±SEM), *P<0.01 sham surgery vs. 2CLP+PBS and **P<0.01 2CLP+PBS vs. 2CLP+δ-PKC TAT.

Additional experiments also demonstrated that δ-PKC levels were detected by Western Blots in BALF from both 2CLP and 2CLP+δ-PKC–TAT treated rats (FIG. 15). As shown in FIG. 16, intra-tracheal administration of the δ-PKC–TAT peptide inhibitor blocks 2CLP-mediated phosphorylation of δ-PKC (Thr 505) in the lung. These experiments show that 2CLP produces (1) pulmonary alterations within 24 hours and (2) activated δ-PKC and δ-PKC phosphorylation in the lung. However, intra-tracheal δ-PKC–TAT can inhibit the sepsis-induced activation of δ-PKC.

Figure 17:
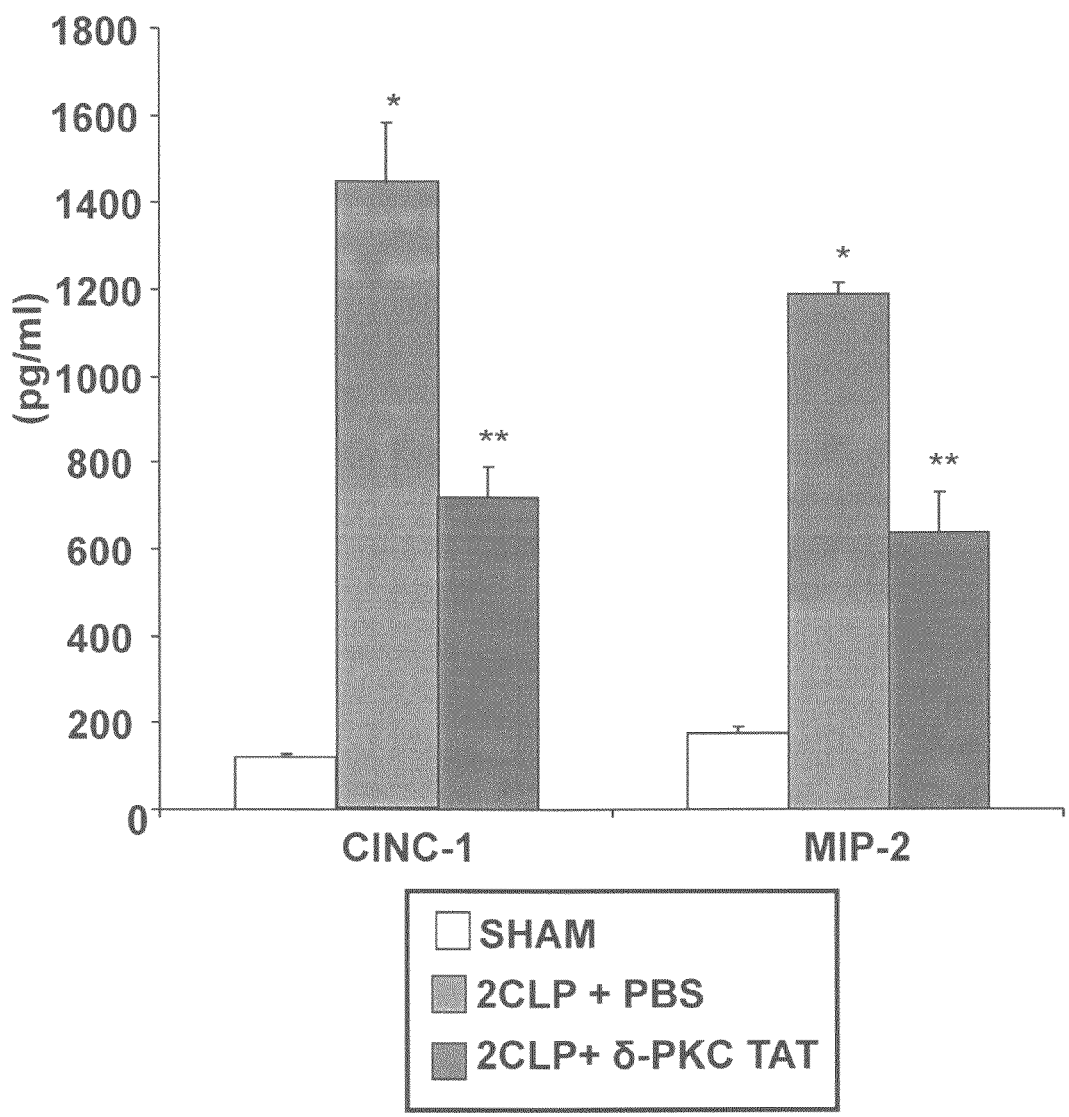
FIG. 17. Intra-tracheal administration of the δ-PKC TAT peptide inhibitor decreases 2CLP-mediated elevations of the chemokines CINC-1 and MIP-2 in the lung. BALF was collected by instilling and withdrawing 1.5 ml of sterile PBS three times from the lungs via an intra-tracheal cannula (24 hrs post 2CLP). CINC-1 and MIP-2 levels are expressed as Mean±SEM (n=8–14) *P<0.01 Sham Surgery vs. 2CLP+PBS, **P<0.01 2CLP+PBS vs. 2CLP+δ-PKC TAT.
Figure 18:
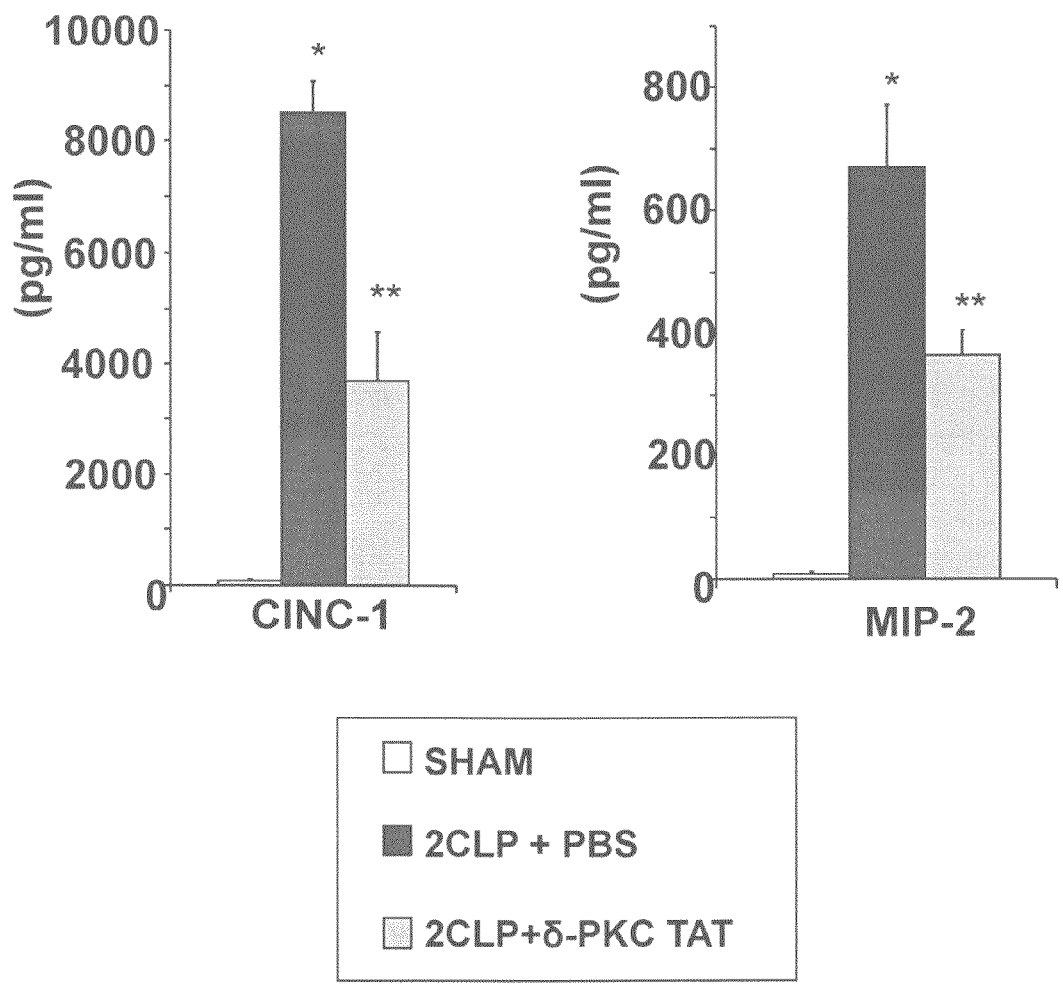
FIG. 18. Intra-tracheal administration of the δ-PKC TAT peptide inhibitor decreases 2CLP-mediated elevations of plasma CINC-1 and MIP-2. Plasma CINC-1 and MIP-2 levels are expressed as Mean±SEM (n=8–14) *P<0.01 Sham Surgery vs. 2CLP+PBS, **P<0.01 2CLP+PBS vs. 2CLP+δ-PKC TAT.
Figure 19:
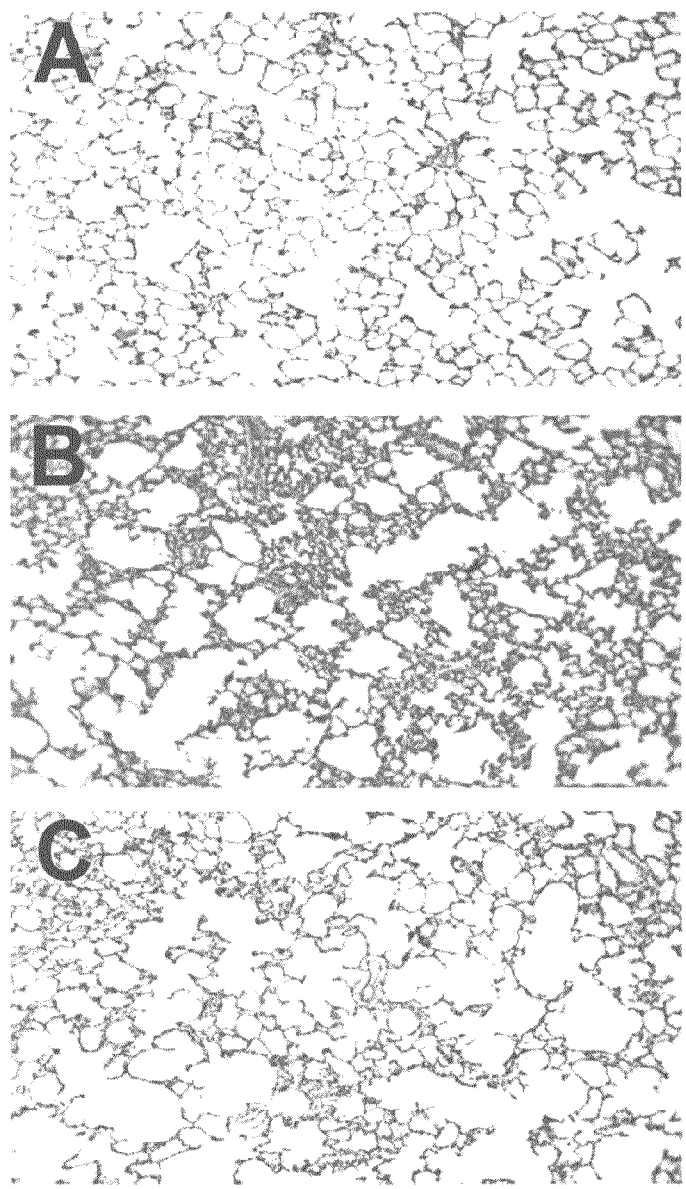
FIG. 19. Intra-tracheal administration of δ-PKC–TAT Peptide inhibitor decreases sepsis-induced lung injury 24 hrs following 2CLP. H & E staining of lung sections obtained from rats 24 hrs post 2CLP or Sham Surgery. Representative sections of (A) Sham surgery, (B) 2CLP+ intra-tracheal administration of PBS, and (C) 2CLP+ intra-tracheal administration of δ-PKC–TAT Peptide Inhibitor. Original magnification 100×.

As discussed in Example 2, 2CLP elevates chemokine levels. Importantly, FIGS. 17 and 18 show that intra-tracheal delivery of the δ-PKC–TAT peptide decreases CINC-1 and MIP-2 in BALF from lungs (FIG. 17) and in plasma (FIG. 18). Thus, sepsis-triggered elevations of BAL fluid and plasma levels of the chemokines CINC-1 and MIP-2 were shown to be δ-PKC dependent. Additionally, FIG. 19 shows that intra-tracheal administration of δ-PKC–TAT peptide inhibitor decreases sepsis-induced lung injury in 24 hrs following 2CLP. This data underscores the ability of δ-PKC–TAT peptide inhibitor to attenuate pulmonary injury.

Figure 20:
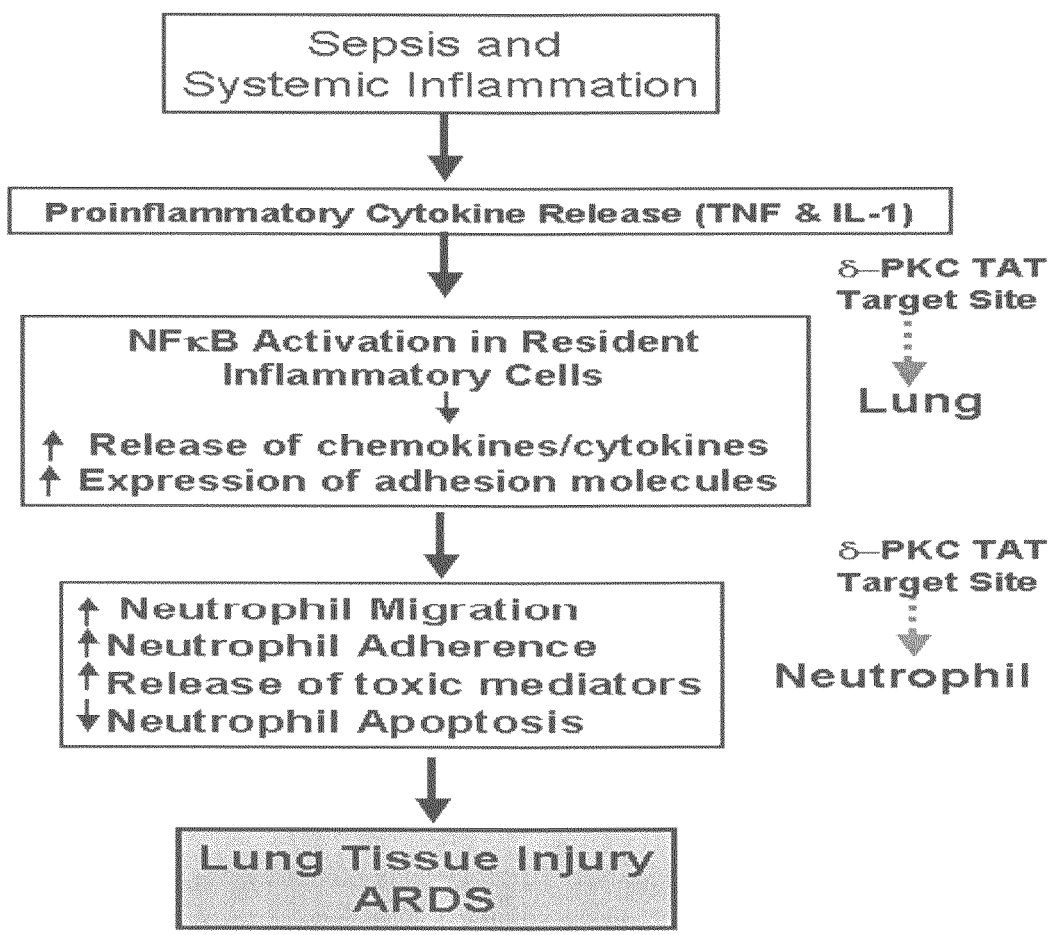
FIG. 20. Model for δ-PKC inhibition leading to a decrease in proinflammatory events in the lung.

Excessive recruitment of activated neutrophils to the lung and subsequent lung injury is one of the hallmarks of ARDS. While neutrophil ingestion and killing of invading microorganisms is critical to host defense, dysregulation of neutrophil function can contribute to tissue damage characteristic of the inflammatory process. Neutrophil dysfunction has an important role in the early course of lung injury and development of respiratory failure through the release of toxic mediators that damage pulmonary tissue. Neutrophil recruitment to the lung, pro-inflammatory responses, and apoptosis are potential therapeutic targets for the treatment of ARDS. In ARDS, there is an intense systemic inflammatory response triggering the release of cytokines and proinflammatory mediators (FIG. 20). In the lung, early response cytokines such as TNF and IL-1 trigger activation of the transcription factor NFκB in resident inflammatory cells such as alveolar macrophages, epithelial and endothelial cells. NFκB regulates gene expression of chemokines, adhesion molecules, and pro-inflammatory and anti-inflammatory cytokines. These pro-inflammatory mediators regulate neutrophil migration, apoptosis, and activation within the lung. Neutrophil dysfunction plays an important role in the early course of lung injury through the release of proteases and oxygen radicals. δ-PKC is an important regulator of cytokine-mediated proinflammatory events in both neutrophils and the endothelium. Inhibition of δ-PKC would prevent cytokine-mediated NFκB activation, pro-inflammatory gene expression and upregulation of adhesion molecules (FIG. 21). Decreased cytokine/chemokine production will attenuate the signaling for neutrophil influx, while decreased expression of adhesion molecules on endothelial cells will reduce neutrophil adherence. δ-PKC also regulates pro-inflammatory and anti-apoptotic signaling in the neutrophil. Inhibition of δ-PKC would inhibit cytokine-mediated oxygen radical production, release of proteases, and decrease neutrophil survival. By inhibiting δ-PKC, cytokine-mediated cellular responses in the lung compartment can be selectively inhibited.

δ-PKC inhibition offers a unique therapeutic strategy because it (1) targets a specific PKC isotype in order to, (2) targets a unique signaling site, and (3) targets activation of a specific neutrophil population and therefore limits lung damage. Thus, control of δ-PKC activity in the lung offers a unique therapeutic intervention that would target multiple sites in the inflammatory response and prevent lung injury. Accordingly, inhibition of δ-PKC should protect host tissue from neutrophil damage and exert lung-protective effects. The availability of a highly selective inhibitor of δ-PKC that is non-toxic and cell-permeant provides means for intra-tracheal administration, aerosol-, liposome-, or nanoparticle-delivery of this agent to decrease neutrophil influx, activation, and prevent lung injury associated with sepsis.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A method of treating lung disease by inhibiting neutrophil activation, comprising intratracheally administering an effective amount of an aerosolized δV1.1 PKC-Tat peptide contained in a pharmaceutically acceptable formulation comprising a propellent, said propellent being selected from the group consisting of halocarbons, hydrocarbons and esters wherein pulmonary neutrophil activation is inhibited at least 2 fold.

2. The method of claim 1, wherein said lung disease is selected from the group consisting of acute lung injury (ALI), adult respiratory distress syndrome, acute trauma, asthma, interstitial lung disease, emphysema, chronic bronchitis, cystic fibrosis, severe acute respiratory syndrome, extracorporeal membrane oxygenation, exposure to irritant gasses, chemicals or toxic substances, and infection.

3. The method of claim 2, wherein ALI follows an event selected from the group consisting of bacterial infection, severe blood loss, thermal injury and blunt trauma.

4. The method of claim 1, wherein said lung disease results in pulmonary infection or inflammation and is caused by thermal injury, smoke inhalation, SARS, anthrax, or radiation exposure.

5. The method of claim 1, wherein pulmonary neutrophil activation is inhibited at least 5 fold.

6. A method of treating lung disease by inhibiting neutrophil activation, comprising intratracheally administering an effective amount of an aerosolized δV1.1 PKC-Tat peptide contained in a pharmaceutically acceptable formulation comprising a propellent, said propellent being selected from the group consisting of halocarbons, hydrocarbons and esters wherein pulmonary neutrophil activation is inhibited at least 2 fold and wherein said compound is linked to a nanoparticle.

7. The method of claim 6, wherein said nanoparticle is a liposome.

* * * * *